US011432720B2

(12) United States Patent
Martie et al.

(10) Patent No.: US 11,432,720 B2
(45) Date of Patent: Sep. 6, 2022

(54) PORTABLE DEVICE HAVING USER INTERFACE FOR VISUALIZING DATA FROM MEDICAL MONITORING AND LABORATORY EQUIPMENT

(71) Applicant: Nicolette, Inc., Los Alamitos, CA (US)

(72) Inventors: Phil Martie, Los Alamitos, CA (US); Michel Mikhael, Los Alamitos, CA (US); Seth Brickman, Los Alamitos, CA (US); Bryan Wilson, Los Alamitos, CA (US); Lee Martie, Los Alamitos, CA (US)

(73) Assignee: Nicolette, Inc., Los Alamitos, CA (US)

( * ) Notice: Subject to any disclaimer, the term of this patent is extended or adjusted under 35 U.S.C. 154(b) by 0 days.

(21) Appl. No.: 16/104,888

(22) Filed: Aug. 18, 2018

(65) Prior Publication Data

US 2019/0053706 A1 Feb. 21, 2019

Related U.S. Application Data

(60) Provisional application No. 62/547,592, filed on Aug. 18, 2017.

(51) Int. Cl.
*A61B 5/00* (2006.01)
*G16H 40/67* (2018.01)
(Continued)

(52) U.S. Cl.
CPC .......... *A61B 5/0004* (2013.01); *A61B 5/0022* (2013.01); *A61B 5/742* (2013.01);
(Continued)

(58) Field of Classification Search
CPC ... A61B 5/0004; A61B 5/0022; A61B 5/0205; A61B 5/7275; A61B 2503/045;
(Continued)

(56) References Cited

U.S. PATENT DOCUMENTS

| 7,751,892 B2 * | 7/2010 | Peterson | A61N 1/37247 |
| | | | 607/30 |
| 2003/0046113 A1 * | 3/2003 | Johnson | G06Q 50/24 |
| | | | 705/3 |

(Continued)

OTHER PUBLICATIONS

Portet F. et al., "Automatic generation of textual summaries from neonatal intensive care data," Artificial Intelligence, vol. 173, Issues 7-8, May 2009. (Year: 2009).*

(Continued)

*Primary Examiner* — Jennifer Mehmood
*Assistant Examiner* — Donna J. Ricks
(74) *Attorney, Agent, or Firm* — Cooley LLP

(57) ABSTRACT

A wireless device for facilitating visualization of a state of a patient being monitored by monitoring equipment. The device includes a wireless network interface, a camera, and a touch-sensitive display. A processor is in communication with the wireless network interface, the camera, a memory and the touch-sensitive display over a system bus. The device wirelessly receives data representative of a state of a first physiological parameter of a patient over a time interval. The visualization data includes a plurality of visualization data values, each of the visualization data values being generated by a data visualization module of the data visualization server from multiple values of machine data produced by the monitoring equipment in connection with monitoring the first physiological parameter. A first portion of a monitoring screen displayed by the device includes a graphical representation of the visualization data over the time interval along with or more range indicators.

22 Claims, 28 Drawing Sheets

(51) Int. Cl.
*G16H 50/30* (2018.01)
*A61B 5/0205* (2006.01)

(52) U.S. Cl.
CPC .............. *G16H 40/67* (2018.01); *G16H 50/30* (2018.01); *A61B 5/0205* (2013.01); *A61B 5/7275* (2013.01); *A61B 2503/045* (2013.01)

(58) Field of Classification Search
CPC ........ A61B 5/742; G16H 50/30; G16H 40/67; G16H 50/20; G16H 10/60; G05F 19/324; G06T 11/206; G06T 2210/41
See application file for complete search history.

(56) References Cited

U.S. PATENT DOCUMENTS

| | | | |
|---|---|---|---|
| 2011/0074788 A1* | 3/2011 | Regan | G06F 19/3418 345/440 |
| 2011/0275940 A1* | 11/2011 | Nims | A61B 5/222 600/483 |
| 2015/0213211 A1* | 7/2015 | Zaleski | G06F 16/9535 715/753 |
| 2016/0224750 A1* | 8/2016 | Kethman | G06F 19/00 |
| 2016/0270719 A1* | 9/2016 | Liu | A61B 5/7425 |
| 2016/0350488 A1* | 12/2016 | Stocker | A61B 5/742 |
| 2017/0091409 A1* | 3/2017 | Jiang | G16H 10/60 |
| 2017/0224920 A1* | 8/2017 | Finan | A61M 5/1723 |
| 2018/0042559 A1* | 2/2018 | Cabrera, Jr. | A61B 5/14532 |

OTHER PUBLICATIONS

T. Fonseca et al., Vital Signs in Intensive Care: Automatic Acquisition and Consolidation into Electronic Patient Records, Feb. 1, 2009, Journal of Medical Systems, 33, 47-57 (2009) (Year: 2009).*

* cited by examiner

LABORATORY STUDIES
1/14/2015 05:42h: WBC:22.7X10*3 Hgb:13.6 Hct:41.0 Plt:192X10^3 S:53 B:1 L:25 M:15 Eo:0 Ba:0 AL:2 Met:2
1/15/2015 04:50h: Na:128 K:5.7 Cl:99 CO2:22.0 BUN:31 Creat:0.5 Gluc:89 Ca:10.0
1/16/2015 05:32h: Na:135 K:3.8 Cl:101 CO2:28.0 BUN:28 Creat:0.4 Gluc:109 Ca:9.4
1/15/2015 04:50h: TBili:0.1 DBili:0.0
1/16/2015 05:32h: TBili:0.1 DBili:0.0
1/15/2015 09:35h: PT:17.1
1/15/2015 09:35h: PTT:34.3

FIG. 7

COMMENTS: Intubated in DR, Curosurf given x3. Has been on invasive ventilation (alternately going from HFOV to SIMV) since birth, with changes of PIE noted early, with unplanned extubation and immediate reintubation x3. Extubated on 1/12/15 to NIMV, but failed and required reintubation. Started on Decadron 1/6/2015 - 1/13/15 for severe lung disease. CXR with severe changes of chronic lung disease, no pneumothorax. Had received levalbuterol dosing for air trapping at referring

FIG. 9

PORTABLE DEVICE HAVING USER INTERFACE FOR VISUALIZING DATA FROM MEDICAL MONITORING AND LABORATORY EQUIPMENT

CROSS-REFERENCE TO RELATED APPLICATIONS

This application claims priority to and the benefit of U.S. Provisional Patent Application No. 62/547,592 entitled PORTABLE DEVICE HAVING USER INTERFACE FOR VISUALIZING DATA FROM MEDICAL MONITORING AND LABORATORY EQUIPMENT, filed Aug. 18, 2017, the disclosure of which is incorporated herein by reference in its entirety.

FIELD

This disclosure relates generally to systems and methods for patient monitoring and for displaying information relating to monitored physiological parameters.

BACKGROUND

Parents and other family members interested in participating in the care of hospitalized newborn infants, such as those receiving care in a neonatal intensive care unit (NICU), currently find it difficult to a) participate in their children's care and b) make competent decisions on their behalf. This is believed to be due to three primary causes.

First, parents are generally unable to understand their baby's health data; that is, the data stored in the baby's electronic health record (E.H.R.). Such E.H.R. data and reports are very difficult to access, comprehend, and make use of for parents and families. This is because families must follow clumsy processes to access E.H.R. data either via hard media like a CD or DVD, or through a portal using their own equipment if it is available to them. This added friction reduces the likelihood parents will access and use data. In addition, parent-facing data in E.H.R. systems is formatted in a way that is difficult to comprehend. Reports are formatted as daily logs, making data impossible to trend or contextualize. Data points are listed absent of explanation of their meaning or collection methodology. Text-based language is written in short hand/abbreviated summaries.

Second, parents often lack the information necessary to successfully navigate the complexity which typically accompanies the care of an infant in a NICU. For example, parents are unexpectedly put into a position of making critical decisions, signing consents, and participating in care for a wide variety of health ailments that they have no previous knowledge of Hospitals provide very little, if any, consumable education materials for their baby's ailments. If parents choose to search for education, it is typically done via web search, e.g. Google, Bing, Yahoo!, etc. Materials found via this method are problematic in a number of ways. For example, it takes many searches over long periods of time to find useful information because parents are not immediately skilled at understanding how to conduct searches. Moreover, sources identified via web searches are not vetted and thus may provide incorrect or outdated materials. Healthcare teams at hospitals will then have to unwind these learnings, and it is possible parents will carry misunderstandings about health topics after the baby has been discharged from the NICU. In addition, because health topics can be complex, a parent may believe they have consumed relevant research, when, even if valid, is not actually relevant to their baby's status or condition. Finally, the most relatable information on the web to a layperson tends to be subjective, typically in the form of stories from other NICU families. While stories can have value at times and within proper context, they are dangerous and can be counterproductive without a balanced, objective source of education from peer-reviewed research.

Third, parents of NICU babies are under a level of extreme anxiety and stress. High levels of anxiety inhibit a person's ability to comprehend and retain information by up to 90%. This results in parent failing to make competent decisions and participate at an adequate level even if they have been orally briefed on how to do so. Further, high levels of anxiety reduce participation levels with parents because of the emotional difficulty associated with witnessing their baby in poor health and not understanding how they can positively affect the baby's outcome.

This suboptimal level of engagement from NICU parents has led to various poor health outcomes. For example, family satisfaction with their NICU experience is low due to lack of communication tools. Engaged parents of early preemies are discharged earlier, but there are very few instances of engagement NICU parents. Moreover, preemie readmission within two weeks of discharge is close to 30%, and parent engagement is shown to reduce the likelihood of readmission. In addition, healthcare costs are substantially greater for preemies than full-term babies, and a significant portion of this is due to parents lacking competency to make efficient healthcare decisions.

SUMMARY

The data visualization and engagement platform described herein is designed to improve the empowerment level of parents with babies in the neonatal intensive care unit (NICU). In one embodiment the platform is comprised of a portable patient data visualization device and supporting infrastructure. The portable patient data visualization device may be implemented using, for example, a specially configured electronic tablet enabling parents to securely access data visualization and other platform components. Such a tablet may be provided to the parents at, for example, the baby's bedside.

In one aspect, the disclosure relates to a wireless device for facilitating visualization of a state of a patient being monitored by monitoring equipment. The device includes a wireless network interface, a camera, and a touch-sensitive display. One or more processors are in communication with the wireless network interface, the camera and the touch-sensitive display over a system bus. A memory of the device includes program instructions which, when executed by the processor, cause the processor to receive, from a data visualization server via the wireless network interface, visualization data representative of a state of a first physiological parameter of a patient over a time interval. The visualization data includes a plurality of visualization data values, each of the visualization data values being generated by a data visualization module of the data visualization server from multiple values of machine data produced by the monitoring equipment in connection with monitoring the first physiological parameter. The one of more processors further cause a monitoring screen to be displayed on the touch-sensitive display where a first portion of the monitoring screen includes a graphical representation of the visualization data over the time interval. One or more range indicators are also displayed on the touch-sensitive display together with the graphical representation of the visualization data so as to convey an indication of stability of the first physiological parameter over the time interval.

When user input corresponding to a change in the time interval is received, via the touch-sensitive display, the processor generates an updated monitoring screen including an updated graphical representation of the visualization data over an adjusted time interval different from the time interval. The processor may also be configured to display, in a second portion of the monitoring screen different from the first portion, an icon corresponding to a laboratory measurement of a second physiological parameter of the patient.

When user input corresponding to selection of the icon associated with the laboratory measurement of the second physiological parameter is received, via the touch-sensitive display, the processor generates a laboratory measurement screen through a graphical representation of laboratory measurement data is rendered.

Various other forms of medical information may be displayed in conjunction with the visualization data derived from monitoring equipment. For example, the processor may be further configured to display medical episode information in conjunction with the graphical representation of the visualization data where the medical episode information indicates the occurrence of a plurality of medical episodes over the time interval. In one particular case the first physiological parameter relates to oxygen saturation and the medical episode information relates to at least one of desaturation episodes, apnea episodes and bradycardia episodes.

In particular applications of the device, the graphical representation of the visualization data may include a plurality of graphical objects respectively corresponding to a plurality of time periods included within the time interval. Each of the graphical objects may information identifying a high value and low value of the physiological parameter over one of the plurality of time periods. A plot or other representation of the occurrence of medical episodes over time may also be superimposed over the plurality of graphical objects in order to intuitively convey additional health status information to a user of the device.

Embodiments of the data visualization and engagement platform may empower parents by providing the following unique features:

1) Visualization of Medical Data: The data visualization components of the platform extract raw data from the baby's E.H.R. and enable it to be visualized in a way that laypeople can understand. In one embodiment this is done in the following ways:

a) Visualization: conversion of raw text and numbers into shapes, colors, and spatial relationships enables efficient, objective communication of complex data sets.

b) Context: adding contextual relationships to data, such as range, trend, related data, risk highlights and remedy information gives meaning to data, which further makes it actionable.

c) Interactivity: allowing users to move and drill deeper into data through touch accelerates comprehension and drives engagement.

2) Automated Curation of Research & Education: The platform automates and improves the discovery process for research and education materials. In one embodiment this is achieved in the following ways:

a) Library Building & Leveling: A library of research and education materials are built and sourced manually and indexed by 1) level of depth and 2) topic.

b) Relevance Filtering: Specific algorithmic rules are used for the baby's data in a given area to suggest the most relevant research, e.g. if a baby's respiratory stability is volatile and support levels are high, education and research regarding respiratory distress syndrome will be suggested.

c) Topic Segmenting: As parents are reviewing each of the topics in a Journey module of the platform, 3) Engagement Tools: In one embodiment the platform provides two specific tools that encourage and reward greater levels of participation from parents.

a) Diary: The Diary enables parents to document their baby's NICU journey with captioned photos, videos, and journal entries, and gives them outputs to share as they see fit with family and friends. The diary pulls simple growth data from the E.H.R. such as height and weight. It also allows parents to log in data as they wish for engagement items such as breast feeding volumes and kangaroo times.

b) Question Generator: Embedded within each NICU topic the parent is viewing, a question generator is available. This achieves three things:
      i) Encourages the act of asking questions, which typically is difficult for parents
      ii) Articulates questions for parents that are tailored to what the baby is experiencing in that moment. This is algorithmically worded based on the baby's E.H.R. data.
      iii) Allows parents to indicate their level of comprehension with the answers they are given by the hospital's healthcare team.

These three tool types work together to synergystically drive greater engagement on all fronts, e.g. consumption of medical data leads to more research and engagement, and engagement in turn leads to greater data consumption. This occurs for at least three reasons:

1) Learning Styles: Learning styles for humans are diverse, falling into seven primary categories: visual, verbal (written & spoken), physical, logical, social, aural, solitary. Three platform components each represent a best-case starting point for each learning style, thus "hooking" and retaining engagement. Visual Data (visual, logical), research & education (verbal, solitary) and engagement (physical, social, aural). Once engaged by their favored means of learning, parents are able to effectively consume all components of their baby's journey.

2) Proximity: The three components are easy to navigate quickly on one screen inside of one application executing on the portable patient data visualization device, enabling more rapid learning and empowered participation. In the current state, consumption of medical data and research of disparate activities that lose meaning because they are not performed cohesively. Single-app proximity drives the greater mutual consumption.

3) Complementary Value: Each of the three components of the application lead to greater use of the other two because they enhance the value. For example, consumable medical data puts context into research and education which allows parents to apply education to their child effectively. Likewise, parents are driven to document their journey when they are confident in their ability to competently participate. Further, the enjoyment of documentation via the Diary module compels them to learn more and consume more data so that they can document more events via media or journal entry.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 7 illustrates the type of data conventionally produced by a laboratory performing measurements of the biochemical characteristics of a patent.

FIG. 9 illustrates exemplary manually-entered data relating to one or more events occurring in the care of a patient.

Figure 1:
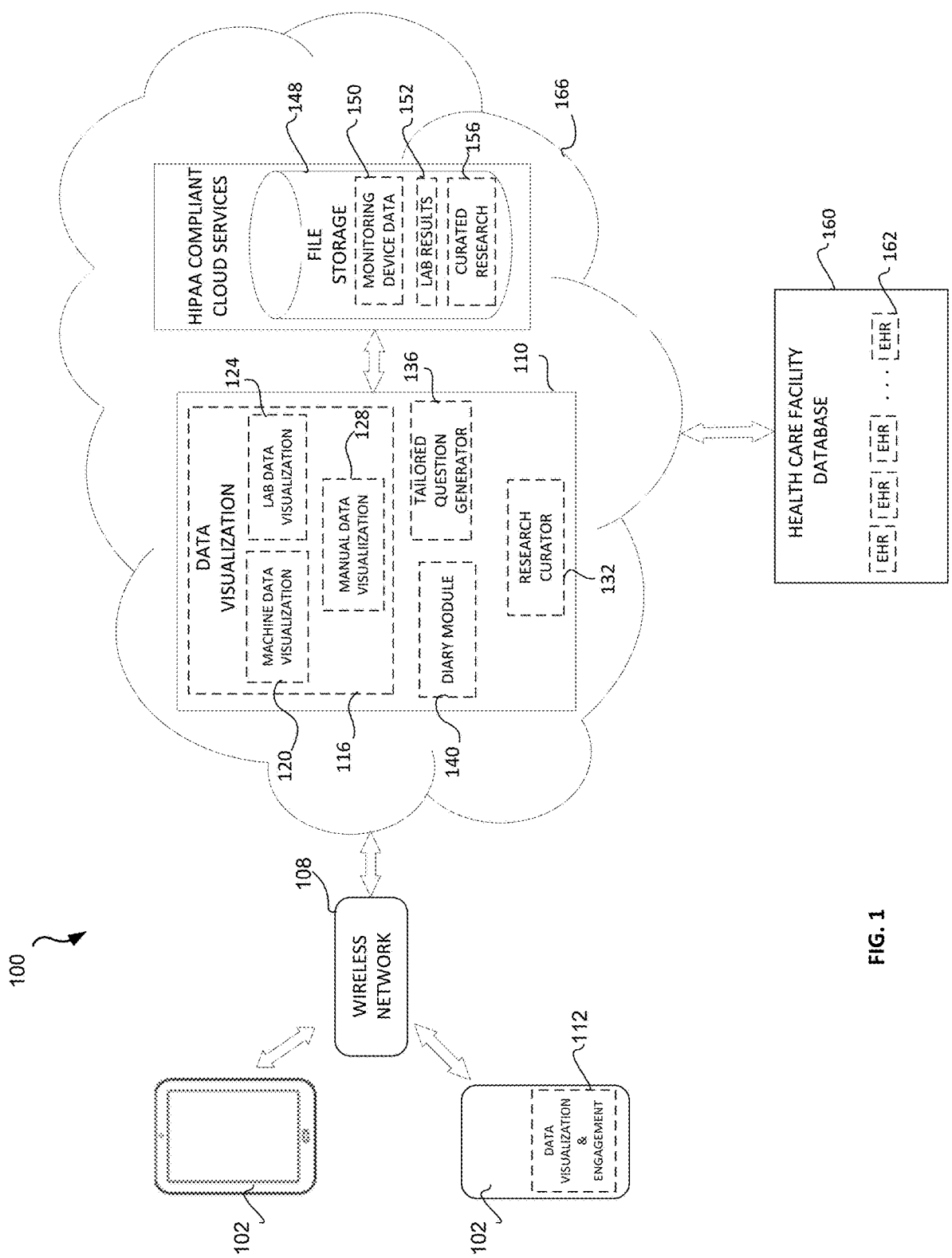
FIG. 1 illustrates a data visualization and engagement platform in accordance with the disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments. Also, common but well-understood elements that are useful or necessary in a commercially feasible embodiment are often not depicted in order to facilitate a less obstructed view of these various embodiments.

DETAILED DESCRIPTION

System Overview and Architecture

Attention is now directed to FIG. 1, which illustrates a data visualization and engagement platform 100 in accordance with the disclosure. As shown, the system includes a plurality of portable patient data visualization devices 102 in communication with a data visualization server configuration 110 via a wireless network 108. As shown, each user device 102 may include a data visualization and engagement module 112 configured to facilitate visualization of, for example, trends and other metrics algorithmically derived from machine-generated patient monitoring data and laboratory results. The module 112 also serves to render curated research relevant to the patient being monitored as well as interactive content intended to drive engagement of the parent or other interested party associated with the patient.

The data visualization server configuration 110 may include, for example, a data visualization module 116 including a machine data visualization module 120, a lab data visualization module 124 and a manual data visualization module 128. The server configuration 110 also includes a research curator 132, a tailored question generator 136 and a diary module 140. Associated with the server configuration 110 is file storage 148 containing machine-generated data 150 produced by patient monitoring equipment, patient lab results 152 and curated research 156. In one embodiment the machine generated monitoring device data 150 and patient lab results 152 may be obtained from, for example, a healthcare facility database 160 containing an E.H.R. 162 corresponding to a monitored patient.

In the embodiment of FIG. 1, the data visualization server configuration 110 and associated file storage 148 may be implemented using "cloud" computing capabilities 166. As is known, cloud computing may be characterized as a model for facilitating on-demand network access to a shared pool of configurable computing resources (e.g., networks, servers, storage, applications, and services) that can be rapidly provisioned and released with minimal management effort or service provider interaction. Cloud systems tend to automatically control resource use by utilizing some form of metering capability with respect to, for example, storage, processing, bandwidth, and active user accounts. Various cloud service models are possible, including cloud software as a service (SaaS), cloud platform as a service (PaaS), and cloud infrastructure as a service (IaaS). In one embodiment the server configuration 110 and associated data storage 148 operates through a Microsoft® Azure cloud. Of course, in other embodiments some or all of the platform may be implemented using other cloud environments such as, for example, an Amazon® Web Service Cloud or another third party cloud.

In other embodiments the data visualization server configuration 110 may be implemented by using on-premise servers and other infrastructure rather than by using cloud-based services. Alternatively, hybrid implementations of the server configuration 110 including a combination of on-premise and cloud-based infrastructure are also within the scope of the present disclosure.

Figure 2:
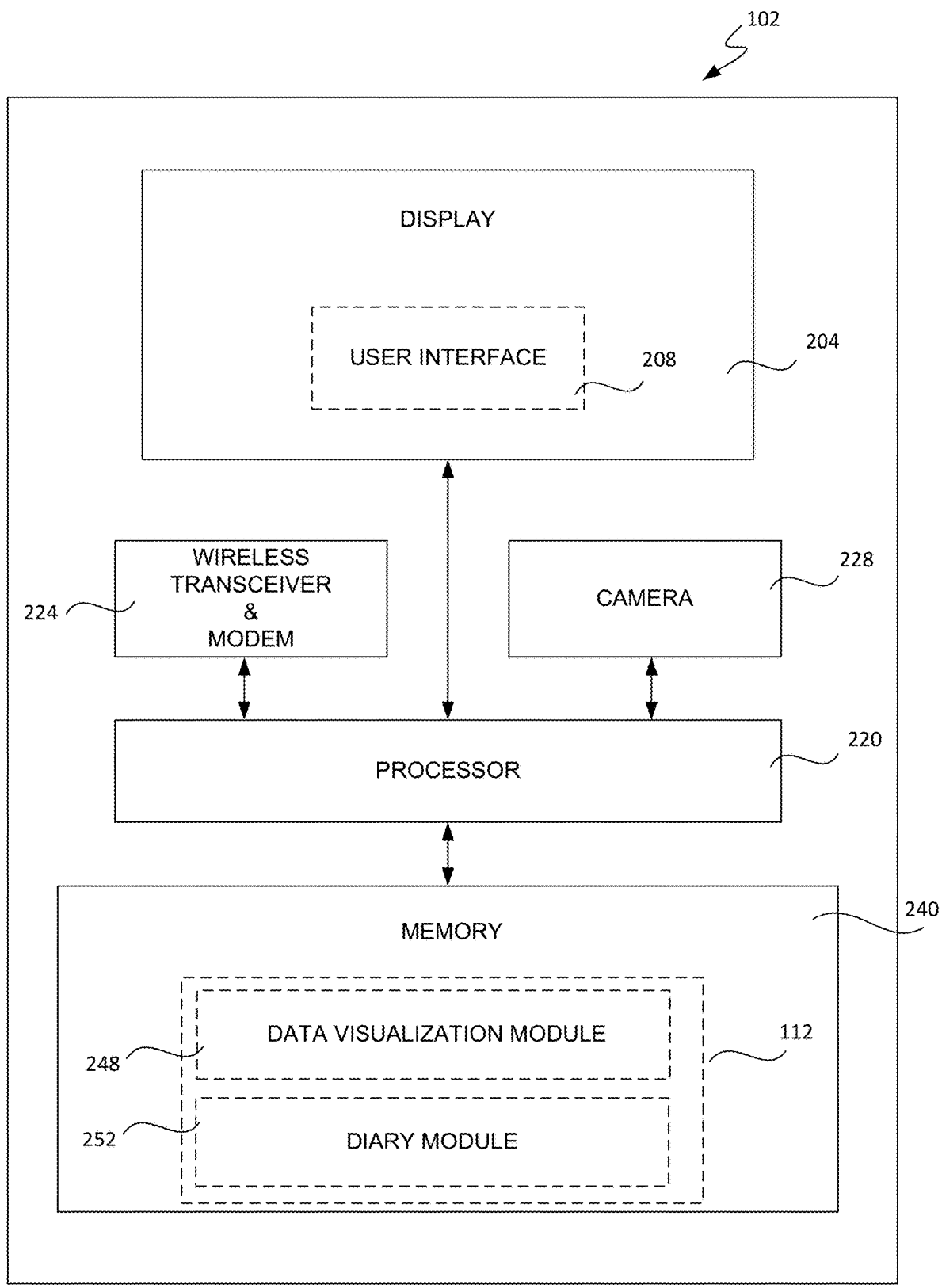
FIG. 2 includes a block diagram representation of one embodiment of a portable patient data visualization device implemented an electronic tablet having wireless communications capability.

During operation of the platform 100, the data visualization module 116 executes algorithms to synthesize trend data and other metrics from, for example, the machine-generated monitoring device data 150 and lab results 152 in order to provide visualization data requested by the portable patient data visualization devices 102. As is discussed below, such visualization data provides parents or other parties involved in the care of a patient, such as an infant in a NICU, an opportunity to participate in the patient's care and make competent decisions on their behalf Attention is now directed to FIG. 2, which includes a block diagram representation of one embodiment of the portable patient data visualization device 102, in this case an electronic tablet having wireless communications capability. It will be apparent that certain details and features of the device 102 have been omitted for clarity, however, in various implementations, various additional features of an electronic tablet as are known will be included. The device 102 is in communication with the server configuration 110 via a communications link which may include, for example, the Internet, the wireless network 108 and/or other wired or wireless networks. The device 102 includes a processor 220 operatively coupled to a touch-sensitive display 204 configured to present a user interface 208. In other embodiments the user interface 208 may include a physical keypad or keyboard, audio input device and/or any other device capable of receiving user input or instructions. The device 102 may also include a wireless transceiver and modem 224, a camera 228, and a memory 240 comprised of one or more of, for example, random access memory (RAM), read-only memory (ROM), flash memory and/or any other media enabling the processor 220 to store and retrieve data. In one embodiment the memory 240 stores the data visualization and engagement module 112 and other programs and/or instructions executable by the processor 220. As shown, the data visualization and engagement module 112 includes a data visualization module 248 and a diary module 252.

Exemplary System Operation and Parent Interface

Figure 3B:
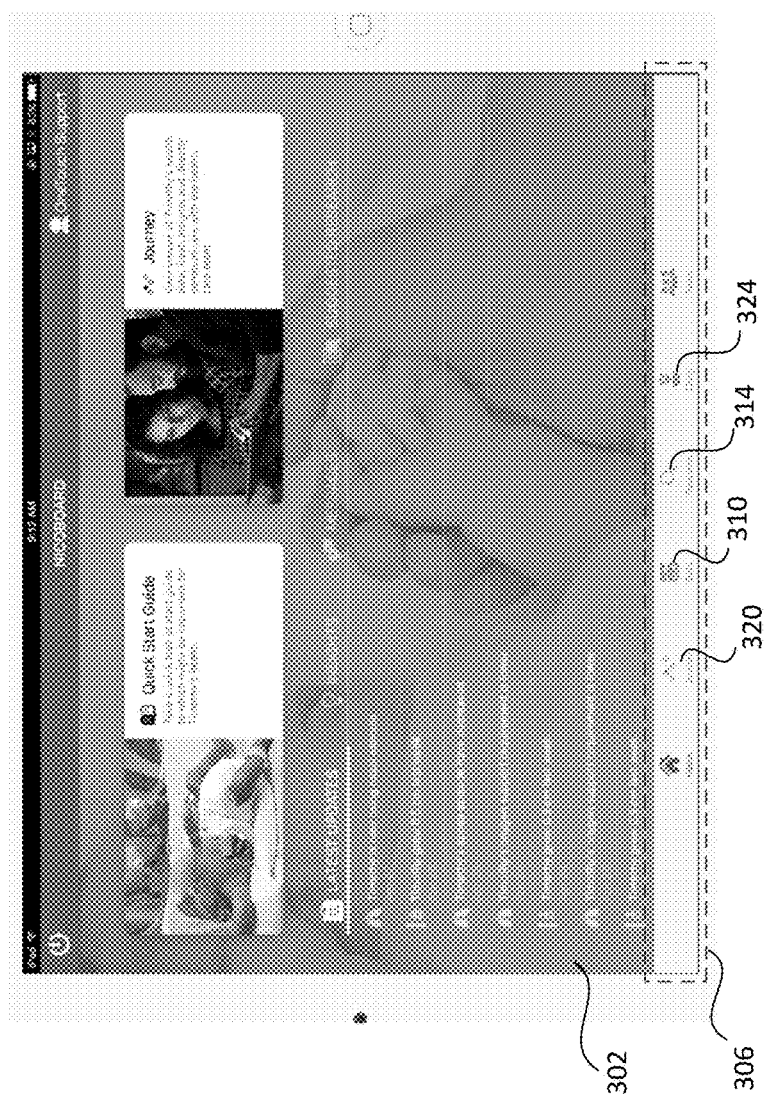
FIG. 3B is an exemplary screen shot of a home screen through a user interface 208 of a portable patient data visualization device.
Figure 3A:
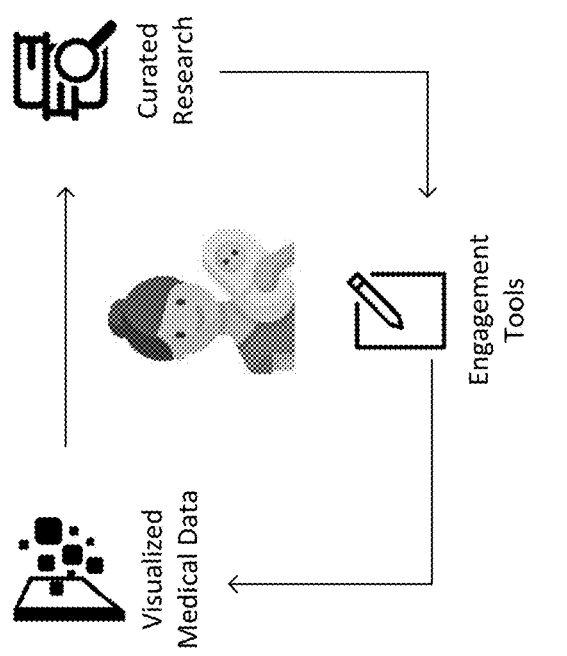
FIG. 3A provides an illustrative representation of the manner in which visualized medical data, curated research and engagement tools accessed through a portable patient data visualization device may collectively empower a patient's parents or caregiver to make confident decisions in short timeframes and participate more competently in their baby's NICU care.

Turning now to FIG. 3A, an illustrative representation is provided of the manner in which the visualized medical data, curated research and engagement tools accessed through device 102 may collectively empower a patient's parents or caregiver to make confident decisions in short timeframes, participate more competently in their baby's NICU care (e.g. feeding, holding, changing, temperature taking, weighing, bathing, physical therapy, etc.), and enjoy a higher level of satisfaction in their stay.

FIG. 3B is an exemplary screen shot of a home screen 302 generated by the module 112 and presented through the user interface 208. As shown, the home screen 302 includes a menu ribbon 306 including a data visualization icon 310 and a curated research icon 314 through which data visualization and curated research services may be respectively accessed.

The ribbon 306 further includes a journey icon 320 and a diary icon 324 through which a user may access the journey and diary engagement tools described hereinafter.

Figure 4A:
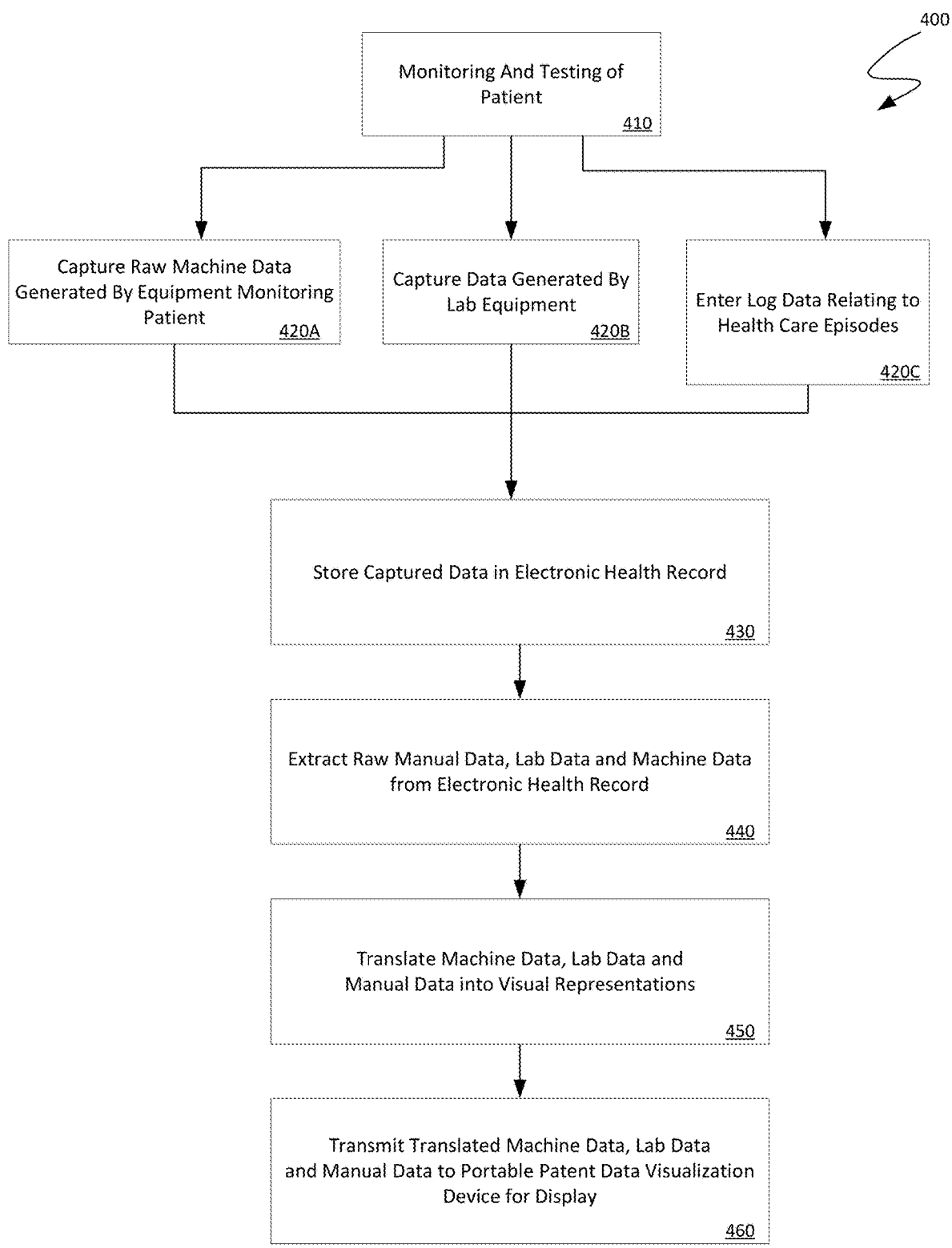
FIGS. 4A and 4B provide an overview of an exemplary process for data visualization in accordance with the disclosure.
Figure 4B:
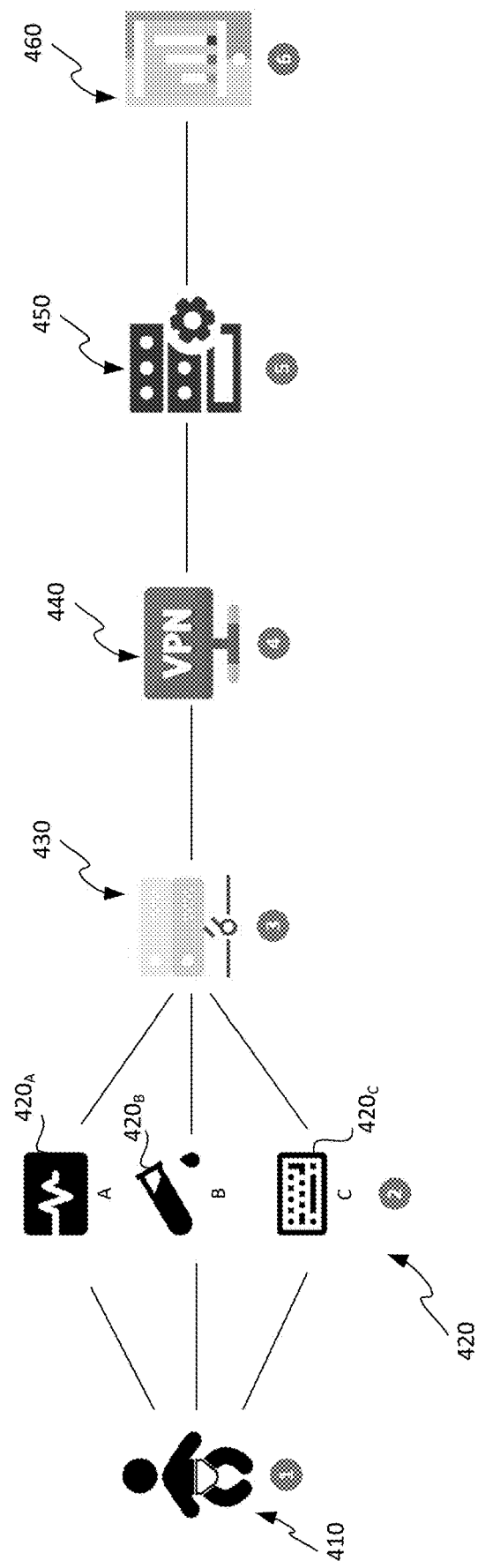

Referring now to FIGS. 4A and 4B, an overview of an exemplary process 400 for data visualization in accordance with the disclosure is provided. The data which is visualized for parents is generated based upon monitoring or testing functions or characteristics of the baby's bodily systems (stage 410). In one embodiment data may be captured in three primary ways (stage 420). Capture methodology and frequency may substantially impact visualization design. For example, data generated by a device connected to the baby, e.g. a pulse oximeter, may be captured (stage 420A). In one embodiment the frequency of data collection is constant although in other embodiments data may be collected at different intervals. In addition, body samples taken from baby and analyzed in lab equipment, e.g. arterial blood gas (ABG), may also be collected (stage 420B). In this case the frequency of collection varies at the provider's discretion. Labs tend to become less frequent as the baby becomes more stable. Finally, healthcare team members may type data directly into the electronic health record, e.g. apnea episodes (stage 420C). Frequency of collection varies based on the events manually entered.

Each baby's data is officially recorded and stored in the Electronic Health Record (E.H.R.) (stage 430). All hospitals have an E.H.R. and these serve as the system of record for patient data. Using API integrations, components of the platform 100 extract raw data from the baby's E.H.R. (stage 440). Algorithms executed by the machine data visualization module 120, lab data visualization module 124 and the manual data visualization module 128 translate the baby's raw data into visual representations that are easy to understand for the parent (stage 450). Each type of data (machine, lab, manual entry) has unique processes to visualize an effective, medically credible way. The translated data, which may include trends or metrics, is displayed visually via the user interface 208 for parents using shapes, colors, and spatial relationships to allow fast synthesis of a complex data set (stage 460).

Figure 5:
FIG. 5 illustrates the type of data conventionally provided by patient monitoring equipment in the case of a patient supported by a ventilator.

FIG. 5 illustrates the type of data conventionally provided by patient monitoring equipment, in this case for a patient supported by a ventilator. Such monitoring equipment or machines are typically used to monitor patient stability metrics, also known as vital signs. The machines generally produce data at consistent intervals on a constant basis, e.g. a pulse oximeter generates data with each heartbeat. However, because machines are used to monitor stability, machine data only has value in the moment for parents. Moreover, machine data is generally only summarized in an E.H.R. as a point-in-time value, hence parents have no way of using the E.H.R. to understand overall stability for an extended period of time or to understand stability trends.

Figure 6:
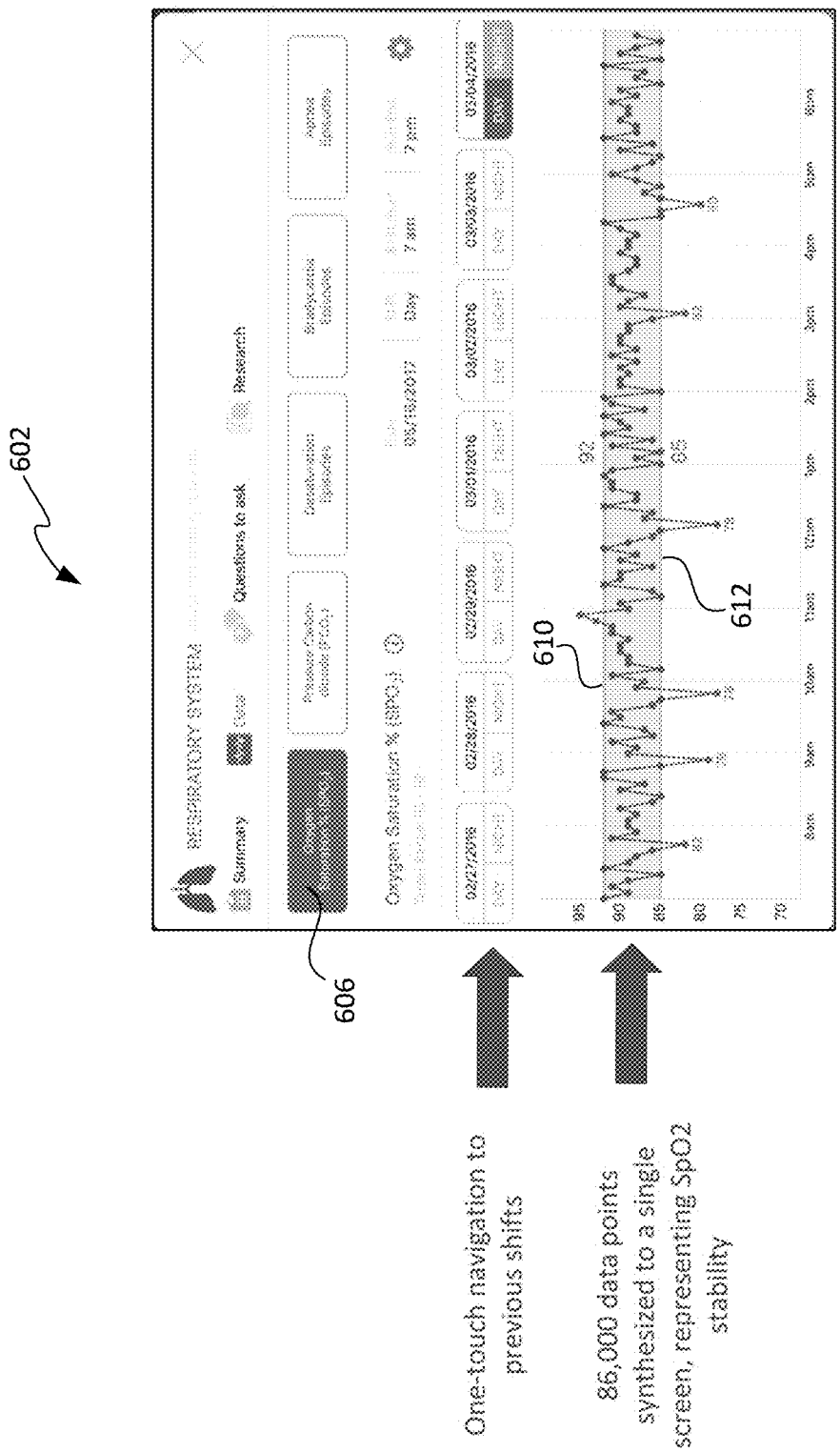
FIG. 6 provides a screen shot of an exemplary respiratory system monitoring screen presented through a user interface of a portable patient data visualization device for the purpose of providing information relating to monitored oxygen saturation percentage.

Attention is now directed to FIG. 6, which provides a screen shot of an exemplary respiratory system monitoring screen 602 presented through the user interface 208 for the purpose of providing information relating to monitored oxygen saturation percentage 606. The monitoring screen 602 may be generated by, for example, the machine data visualization module 120 in cooperation with the data visualization and engagement module 112. In particular, the modules 112 and 120 advantageously aggregate all, or substantially all, machine data points into a plurality of visualization data values. These visualization data values are algorithmically displayed by the monitoring screen 602 as a single-screen visualization that delivers and objectively true portrait of a baby's stability for the shift. The monitoring screen 602 also provides one-touch navigation to previous shifts and includes upper and lower range markers 610 and 612 indicative of a desired range of oxygen saturation percentage.

FIG. 7 illustrates the type of data conventionally produced by a laboratory performing measurements of, for example, the biochemical characteristics of a patent. In general, laboratory analysis may be conducted as needed by clinicians for a variety of reasons, and labs may be run only once or multiple times over a specific timespan to establish a trend or pattern. Typical uses of laboratory data include, for example, diagnosis of symptoms, evaluation of a baby's response to treatment, and establishing a trend for specific health metrics.

Unfortunately, there is little or no context for lab result meanings, e.g. what is being measured, the desired range, the trend, or relationship to treatments. For clinicians with medical expertise these lab results can still be useful, but are not useful to laypeople. Lab results for a specific measure, e.g. PCO2, are not formatted in a way that can be viewed over time to easily observe changes. Moreover, specific measurements are displayed with data points that may not be relevant to the use, e.g. CO2 used to evaluate need for respiratory support but is directly next to glucose level, which is irrelevant to the topic.

Figure 8A:
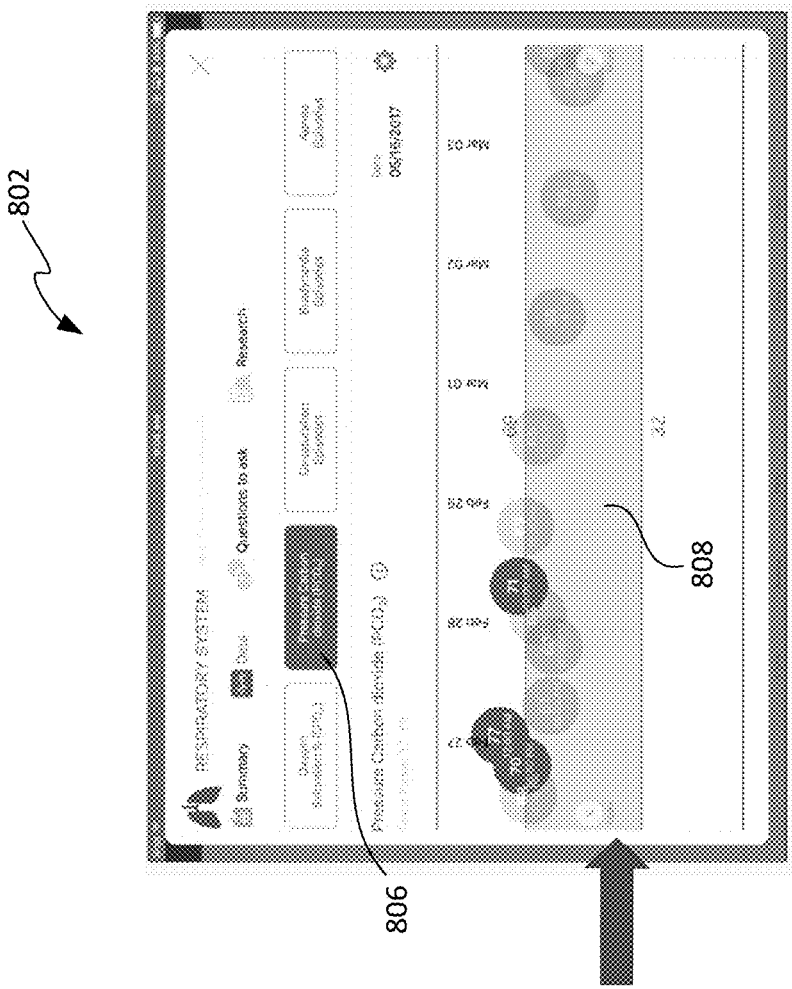
FIG. 8A provides a screen shot of an exemplary respiratory system monitoring screen presented through a user interface of a portable patient data visualization device for the purpose of providing information relating to a carbon dioxide pressure parameter.

FIG. 8A provides a screen shot of an exemplary respiratory system monitoring screen 802 presented through the user interface 208 for the purpose of providing information relating to a carbon dioxide pressure parameter 806. The monitoring screen 802 may be generated by, for example, the data visualization module 116 in cooperation with the data visualization and engagement module 112. The monitoring screen 802 advantageously plots data points for a specific measurement over time, outside of the lab report itself, giving a parent the ability to view trends for one specific measure and to view the measure relative to a desired range 808.

Figure 8B:
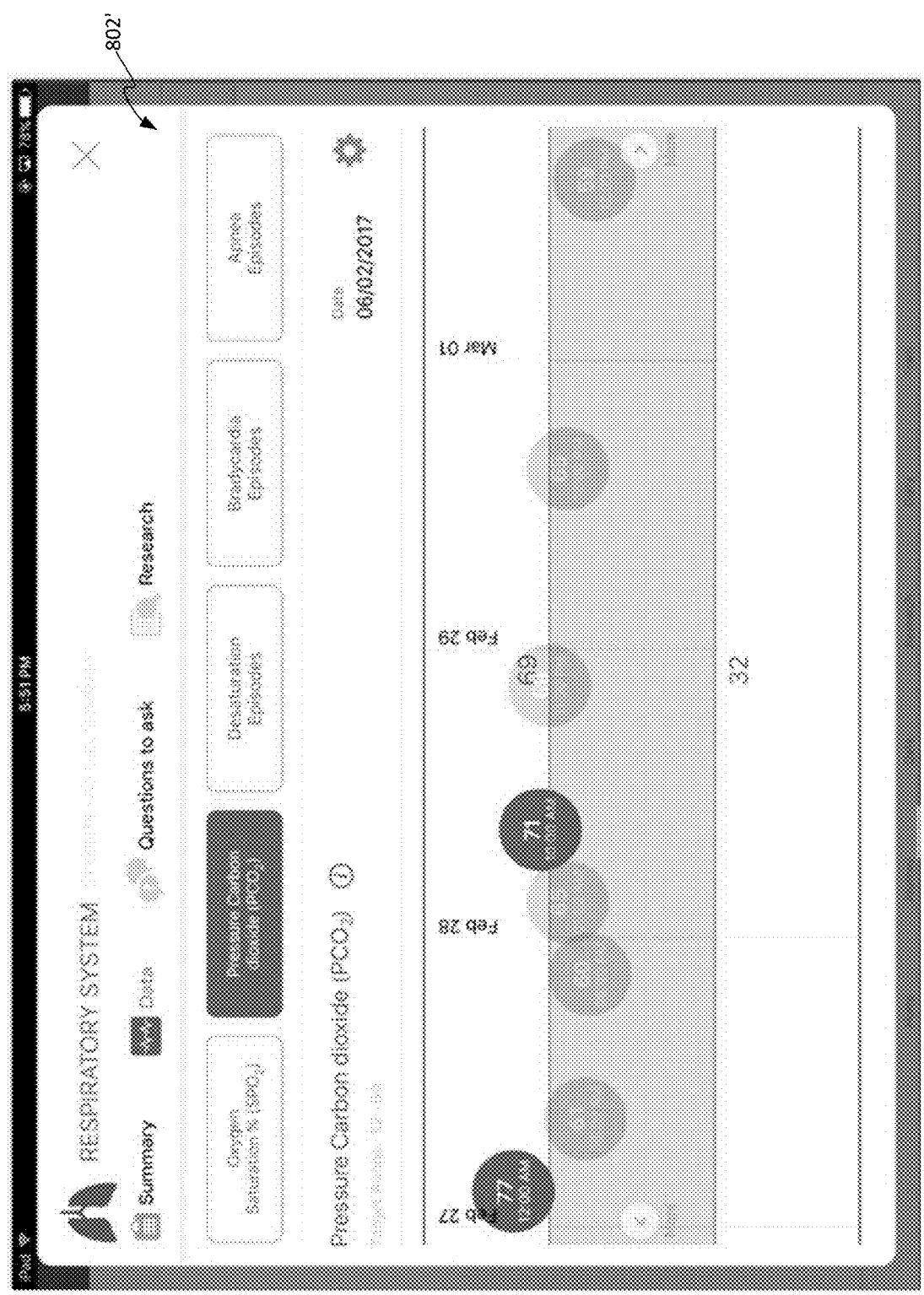
FIGS. 8B and 8C present different magnifications of the exemplary respiratory system monitoring screen of FIG. 8A.
Figure 8C:
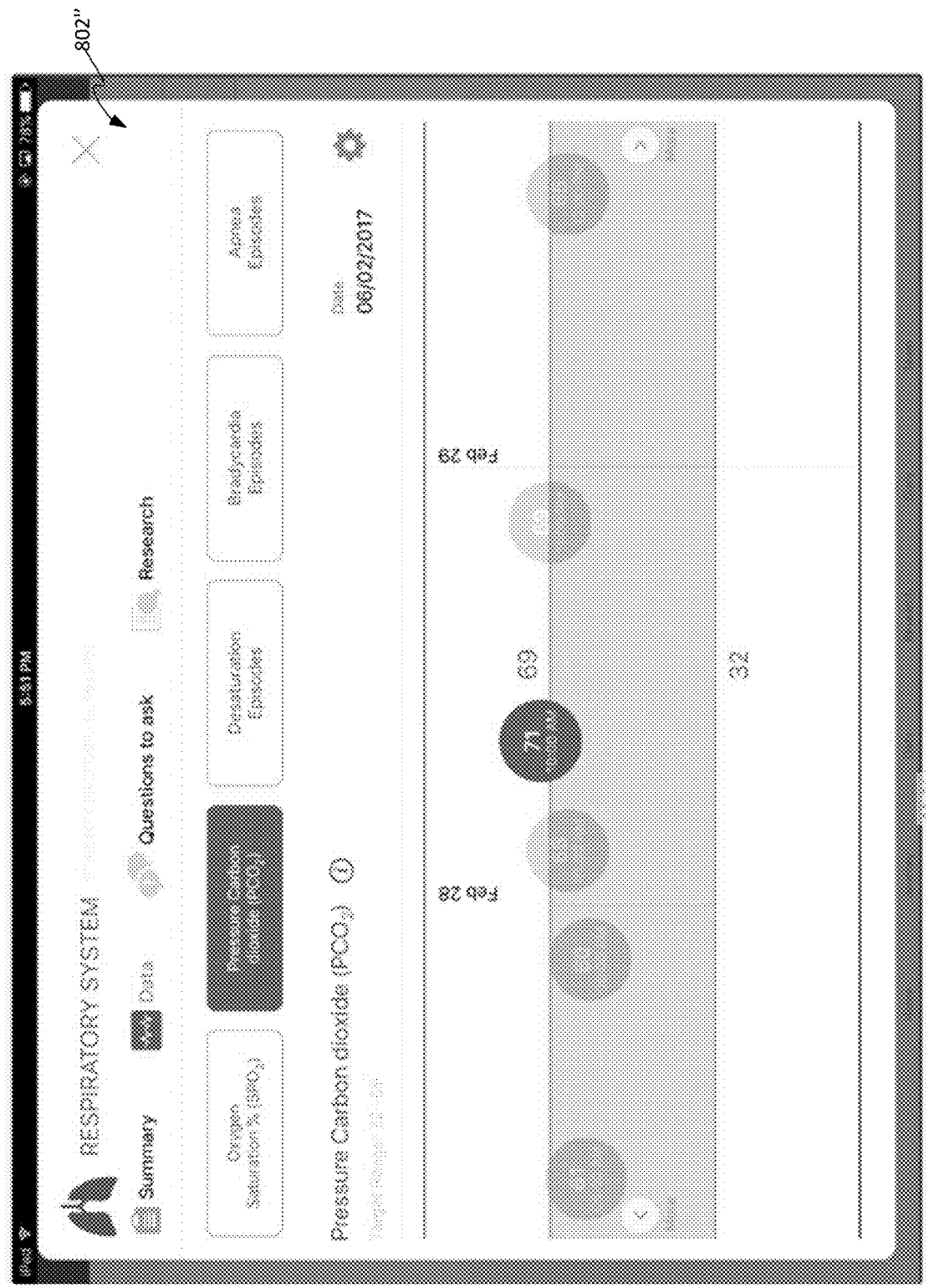

As may be appreciated with reference to FIGS. 8A-8C, the screen 802 enables parents to view longer or short time periods by pinching in or pinching out on the touch-sensitive display 204. As shown, by pinching "out" the touch-sensitive display 204, a user may cause the screen 802 to display the shorter periods depicted in FIGS. 8B and 8C. For example, the user could pinch out the touch-sensitive display 204 a first time to cause the screen 802 of FIG. 8A to transition to the screen 802' of FIG. 8B and then pinch out the out the touch-sensitive display 204 a second time to cause the screen 802' of FIG. 8B to transition to the screen 802" of FIG. 8C.

FIG. 9 illustrates exemplary manually-entered data relating to one or more events occurring in the care of a patient. Manually-entered data is typically event-driven and carries with it both quantitative and qualitative information. Events that drive manual data include medical episodes (e.g. apnea spells) and routine care (e.g. feeding details such as volume, contents, amount by PO vs. gavage). Unfortunately, medical episodes are logged, but no quantitative analysis is available for them, e.g. counts, trends, and insights. Routine care data is generally only available as a table, and formatted next to other health data by date, so no trends or insights are possible.

Figure 10A:
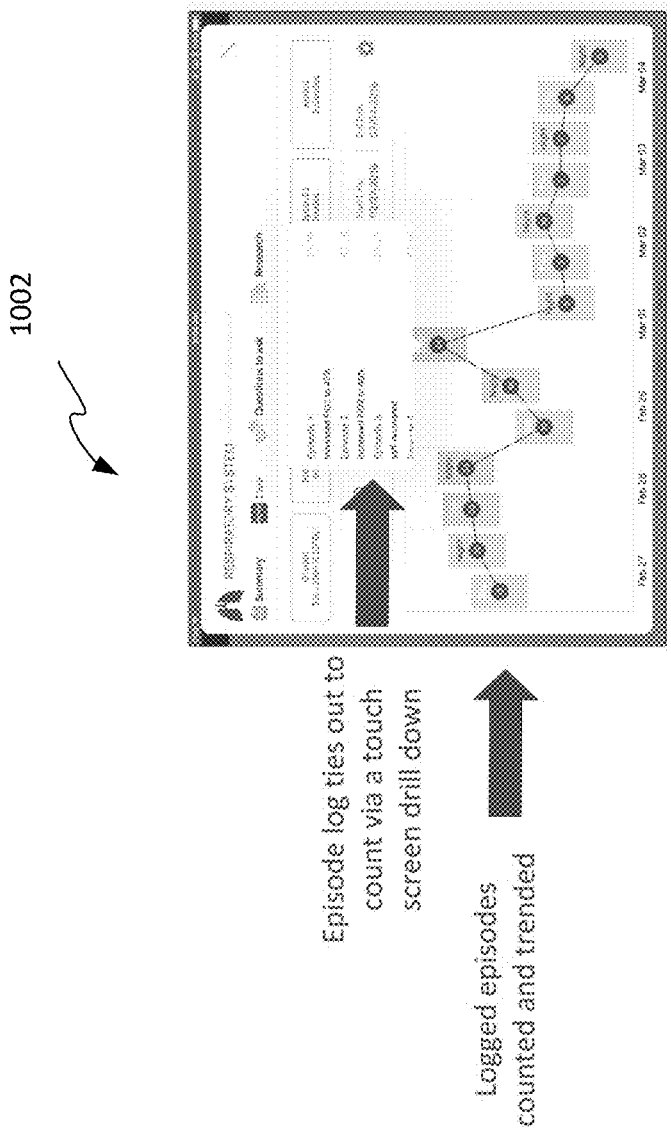
FIGS. 10A-10E provide screen shots of exemplary respiratory system monitoring screens and plots of data visualization values.
Figure 10B:
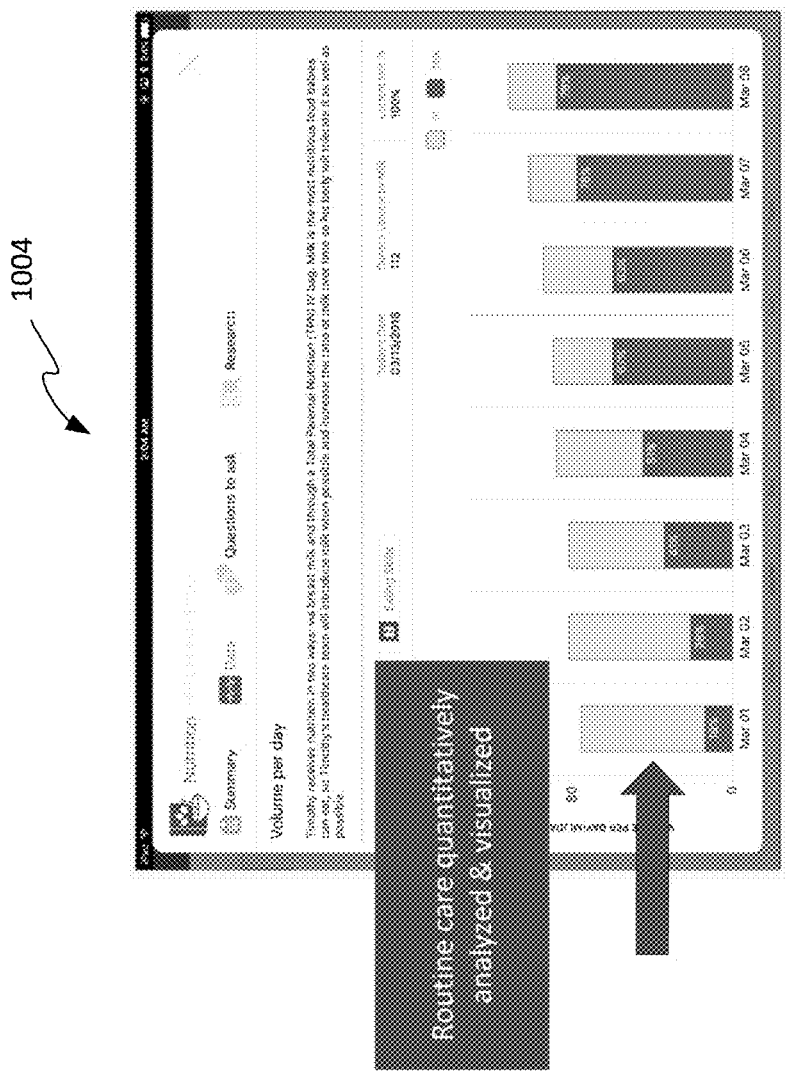

FIG. 10A provides a screen shot of an exemplary respiratory system monitoring screen 1002 presented through the user interface 208 for the purpose of providing information relating to various manually-entered events. Similarly, FIG. 10B provides a screen shot of an exemplary nutrition monitoring screen 1004 presented through the user interface 208 for the purpose of providing information relating to various manually-entered, nutrition-related events. As shown in FIGS. 10A-10B, in each case counts and trends are provided for medical episodes. Both the screens 1002 and 1004 allow parents to drill down via touch and view specific qualitative log information tied to the count for each time period. Moreover, routine care data may be quantitatively analyzed and visualized by time period.

Figure 10C:
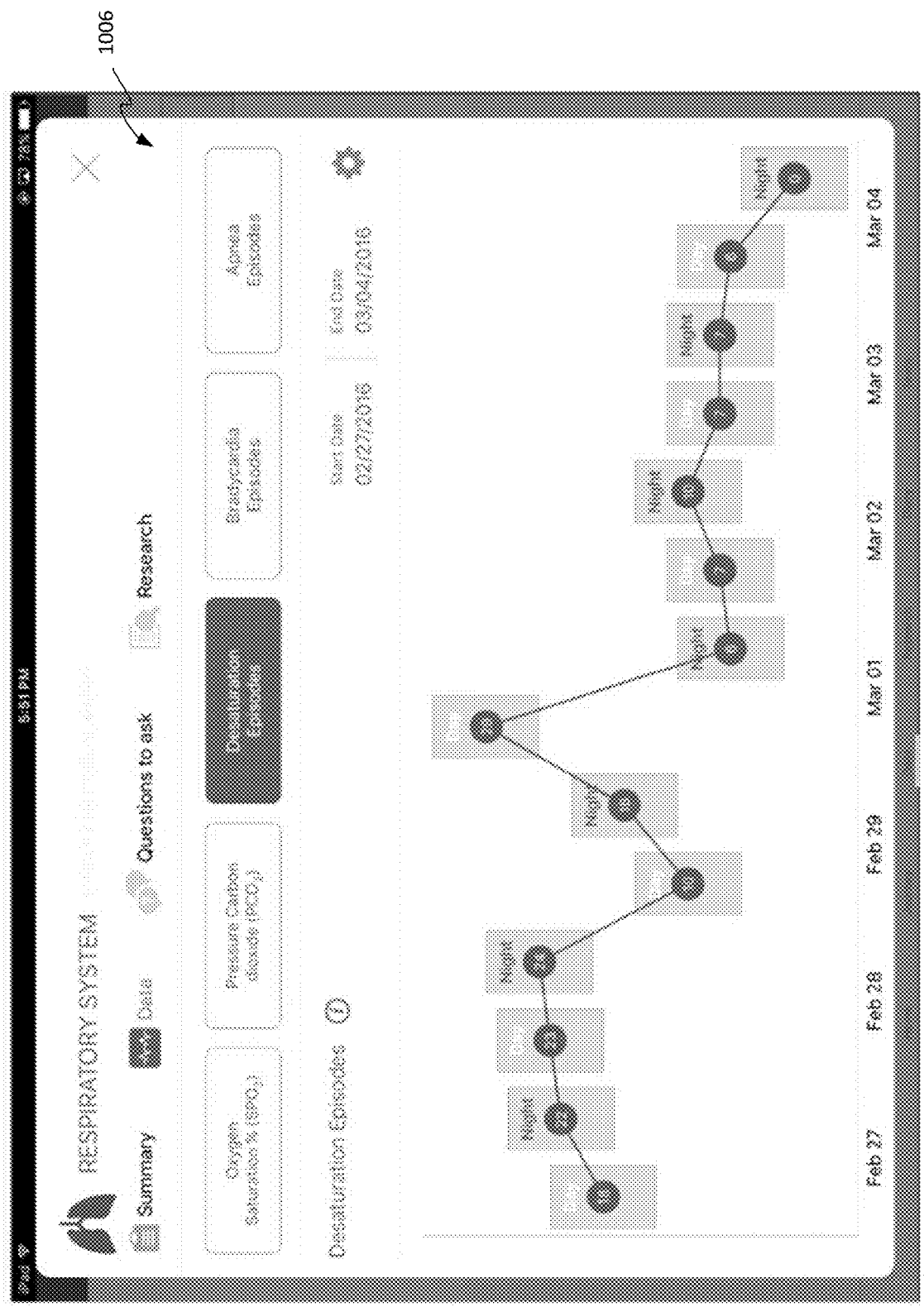
Figure 10D:
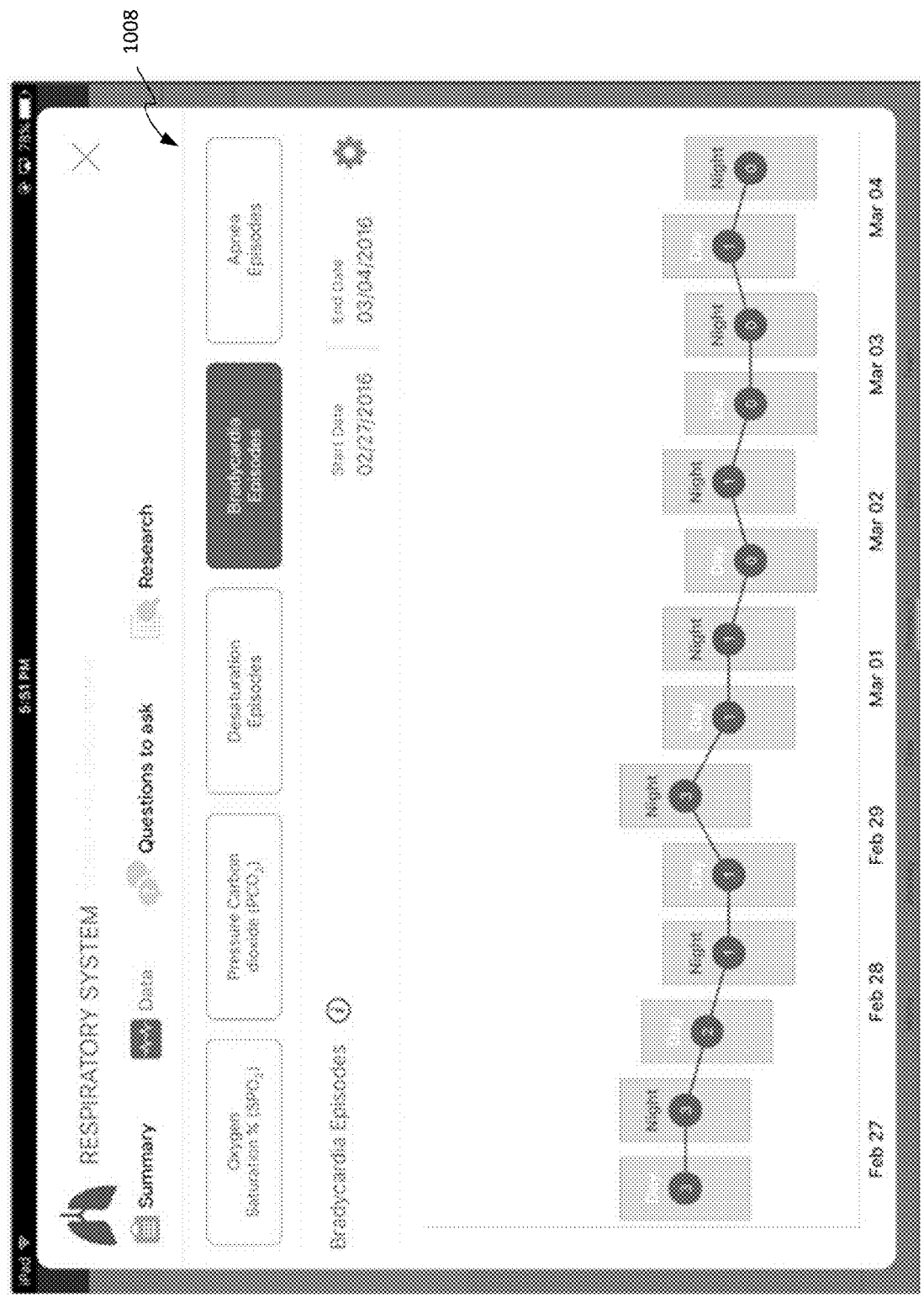
Figure 10E:
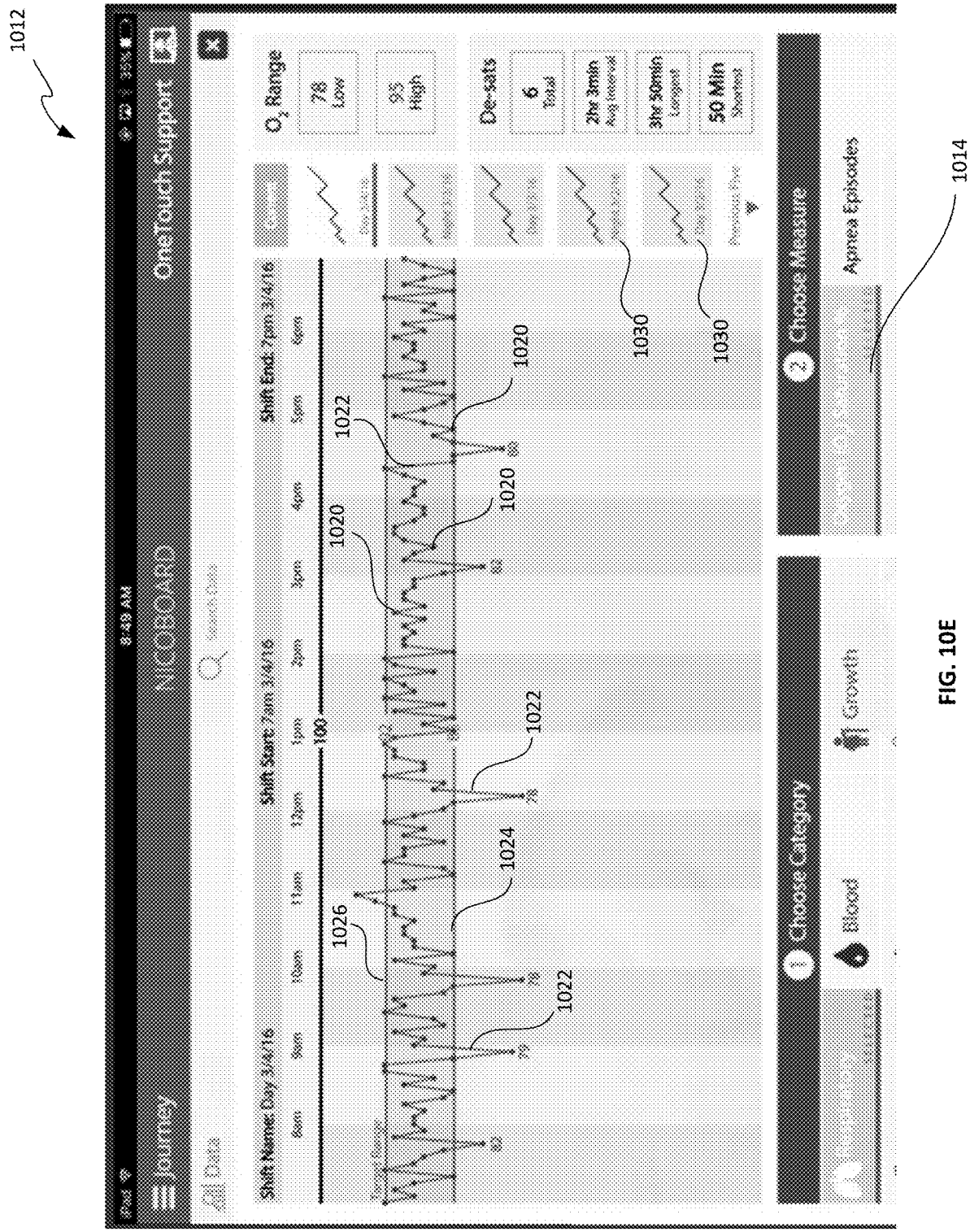
Figure 10F:
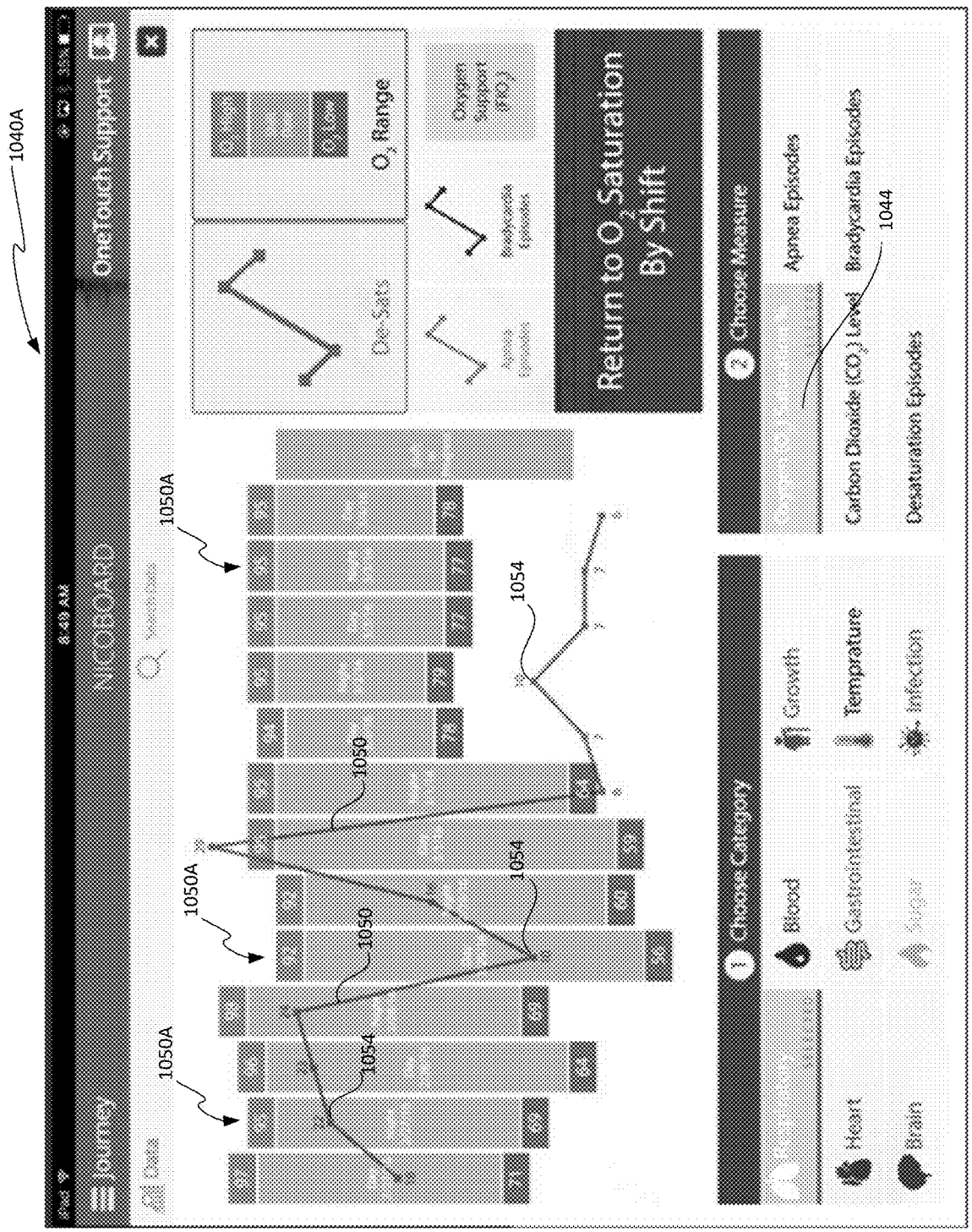
FIGS. 10F-10I, which are screen shots of exemplary respiratory system monitoring screens 1040 presented through the user interface 208 for the purpose of providing information relating to an oxygen saturation parameter 1044 in conjunction with other medical episode information.

FIG. 10C provides a screen shot of an exemplary respiratory system monitoring screen 1006 presented through the user interface 208 for the purpose of providing information relating to exemplary desaturation events over a time period of approximately one week. Similarly, FIG. 10D provides a screen shot of an exemplary respiratory system monitoring screen 1008 presented through the user interface 208 for the purpose of providing information relating to exemplary bradycardia events over a time period of approximately one week FIG. 10E provides a screen shot of an exemplary respiratory system monitoring screen 1012 presented through the user interface 208 for the purpose of providing information relating to a oxygen saturation parameter 1014. The monitoring screen 802 may be generated by, for example, the data visualization module 116 in cooperation with the data visualization and engagement module 112 using machine data values produced by medical monitoring equipment such as, for example, a pulse oximeter. The monitoring screen 802 advantageously plots a plurality of visualization data values 1020 generated from a set of the machine data values by, for example, determining a statistical parameter characterizing the set of machine data values.

As shown in FIG. 10E, the visualization data includes a plot 1022 of the plurality of visualization data values 1020 over which is superimposed a linear representation a low range value 1024 and a linear representation of a high range value 1026. In one embodiment the region between the low range value 1024 and the high range value 1026 bound a desirable range of oxygen saturation and thereby provide a parent with an intuitive means of interpreting the oxygen saturation data associated with their baby.

As may be appreciated from the time scale of FIG. 10E, the plot 1022 spans a duration of approximately 12 hours (e.g., the duration of a typical hospital shift). In one embodiment similar plots of visualization data values corresponding to oxygen saturation of the same baby/patient during other hospital shifts may be displayed by selecting the corresponding thumbnail icon 1030.

Attention is now directed to FIGS. 10F-10I, which are screen shots of exemplary respiratory system monitoring screens 1040 presented through the user interface 208 for the purpose of providing information relating to an oxygen saturation parameter 1044 in conjunction with other medical episode information. As shown, the respiratory system monitoring screens 1040 each depict a plurality of graphical objects 1050 respectively corresponding to a plurality of time periods (i.e., half-days or hospital shifts). Each of the graphical objects 1050 includes information identifying a high value and low value of oxygen saturation for the baby/patient over one of the plurality of hospital shifts.

Figure 10G:
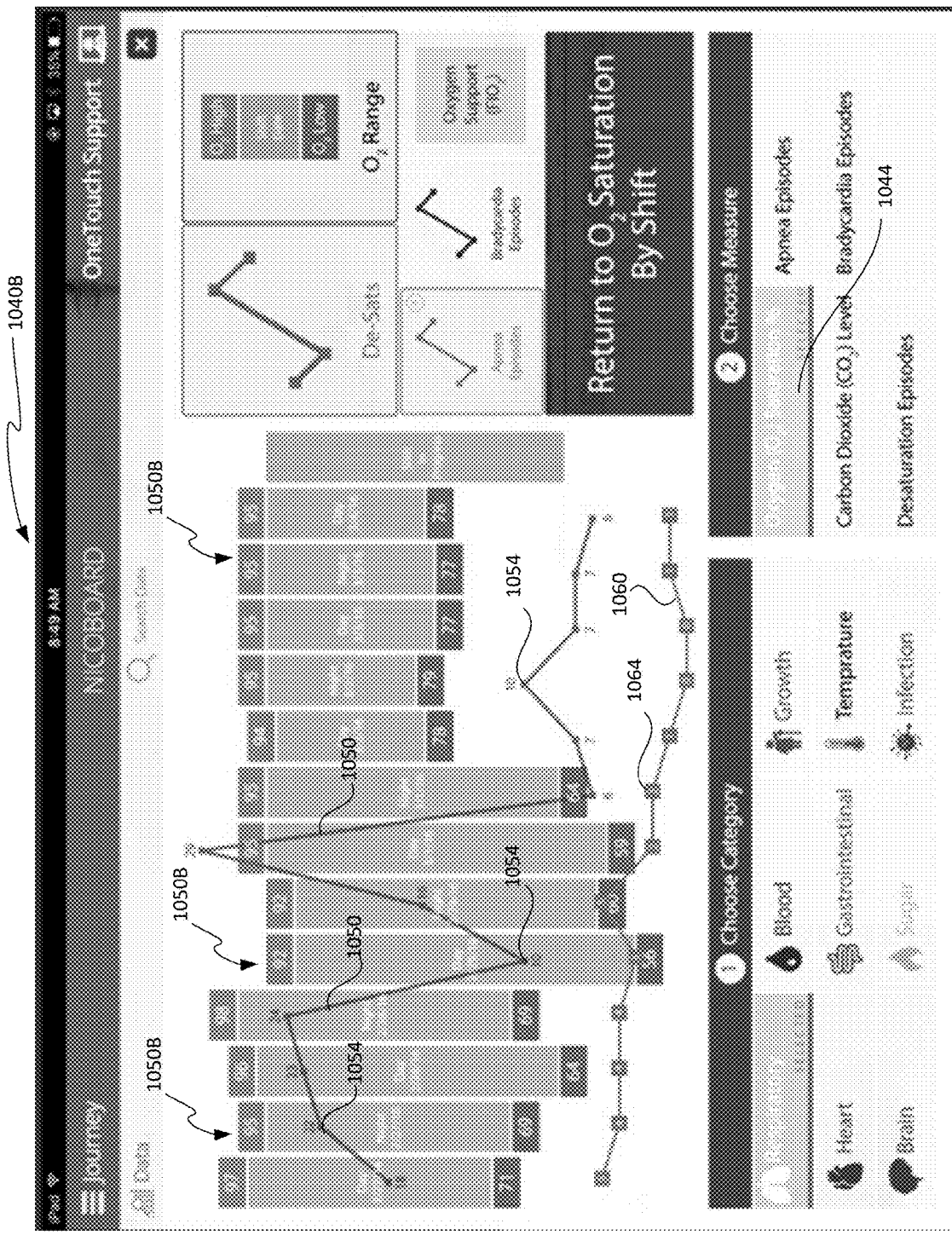
Figure 10H:
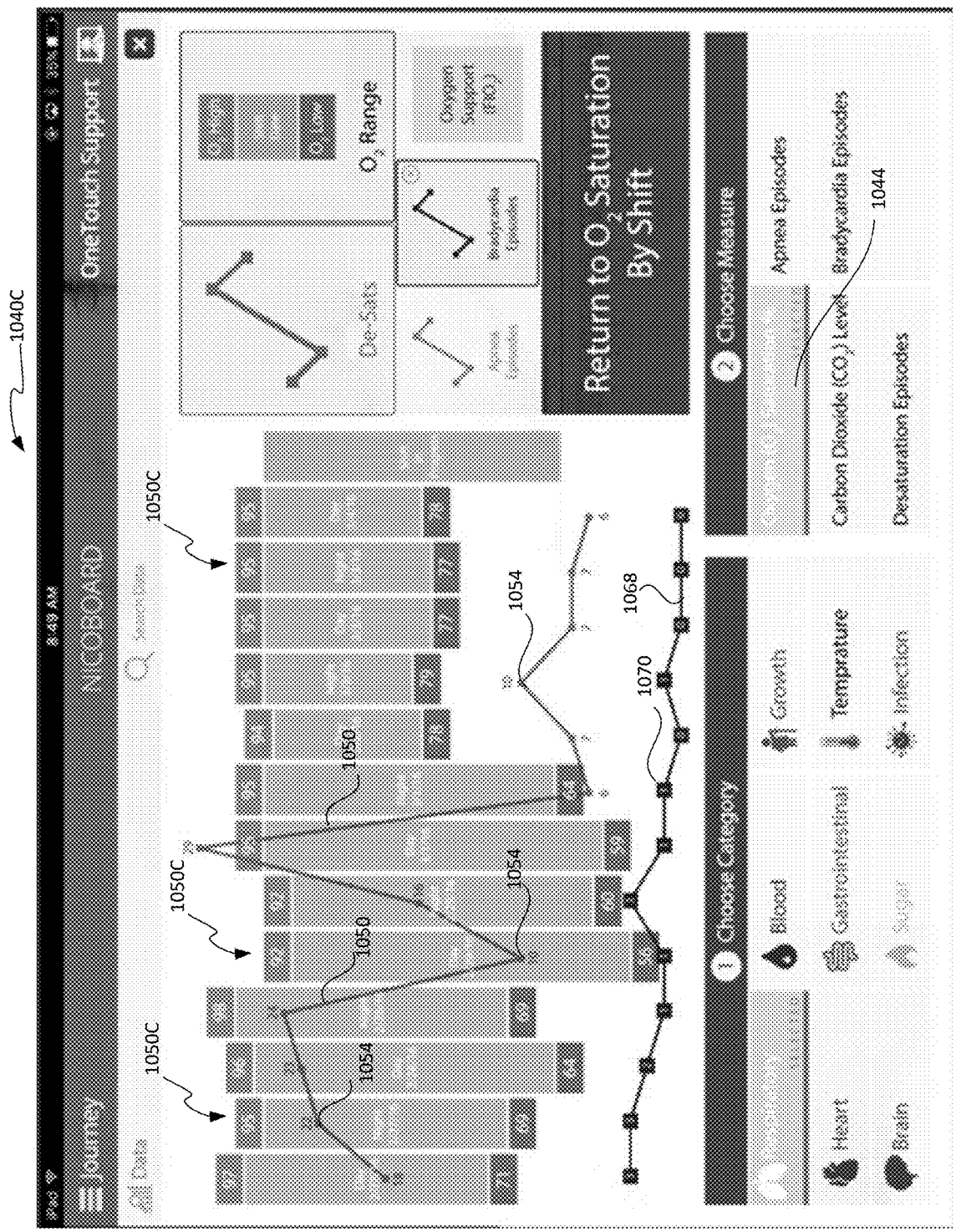
Figure 10I:
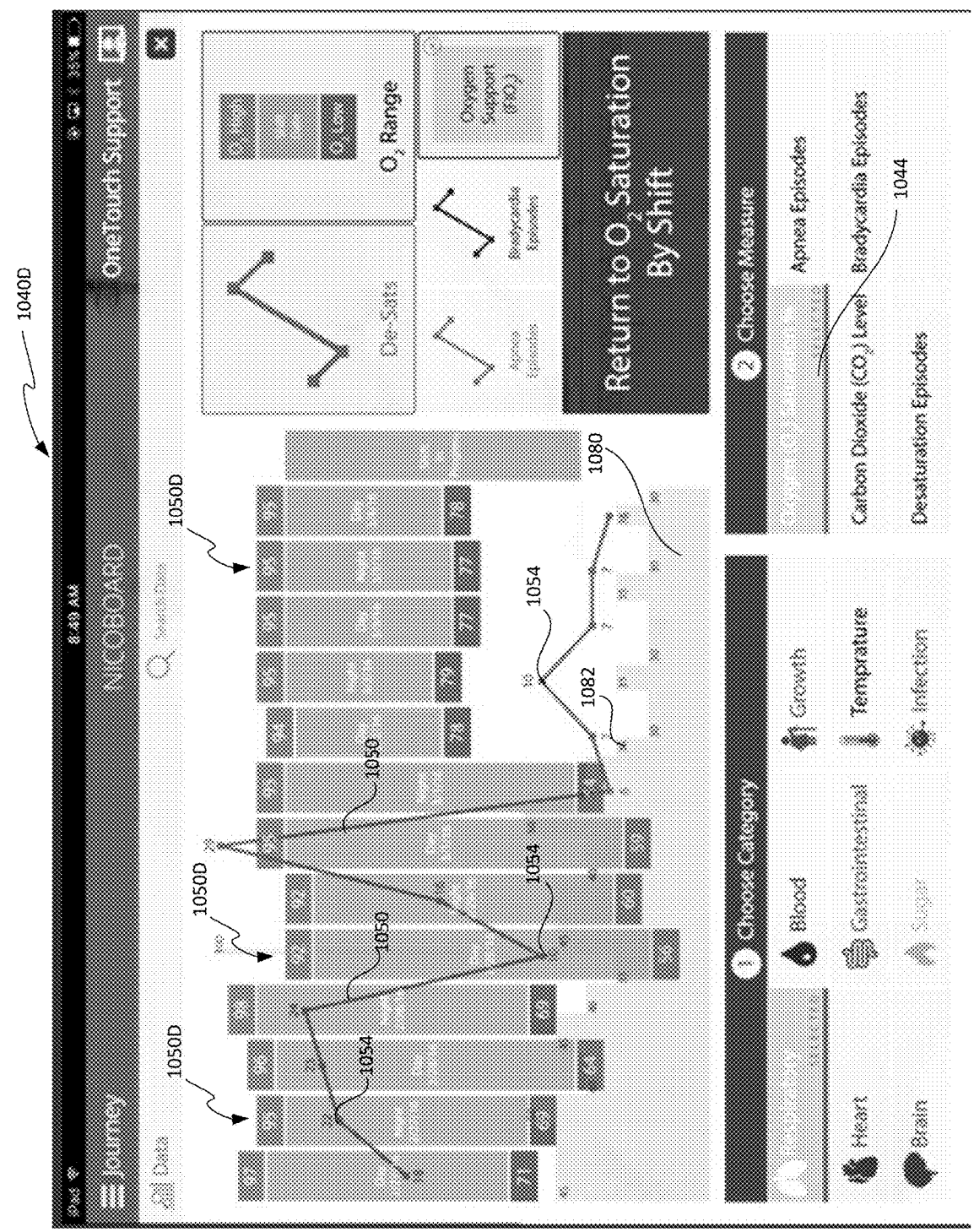

The exemplary respiratory system monitoring screens 1040 of FIGS. 10F-10I also include medical episode information displayed in conjunction with the graphical objects 1050 visually representing oxygen saturation ranges over consecutive hospital shifts. For example, FIG. 10F includes a plot 1054 of the number of oxygen desaturation events per shift 1058 where the plot 1054 is superimposed of the graphical objects 1050. As shown in FIG. 10G, a plot 1060 of the number of apnea episodes per shift 1064 may also be overlaid onto the respiratory system monitoring screen illustrated in FIG. 10F. Alternatively, as shown in FIG. 10H, a plot 1068 of the number of bradycardia episodes per shift 1070 may also be overlaid onto the respiratory system monitoring screen illustrated in FIG. 10F. Of course, medical episodes and related information may also be represented using other graphical techniques. For example, as shown in FIG. 10I, a partially see-through graphical overlay 1080 representative of the number of oxygen support episodes per shift 1082 may also be overlaid onto the respiratory system monitoring screen illustrated in FIG. 10F.

Figure 11A:
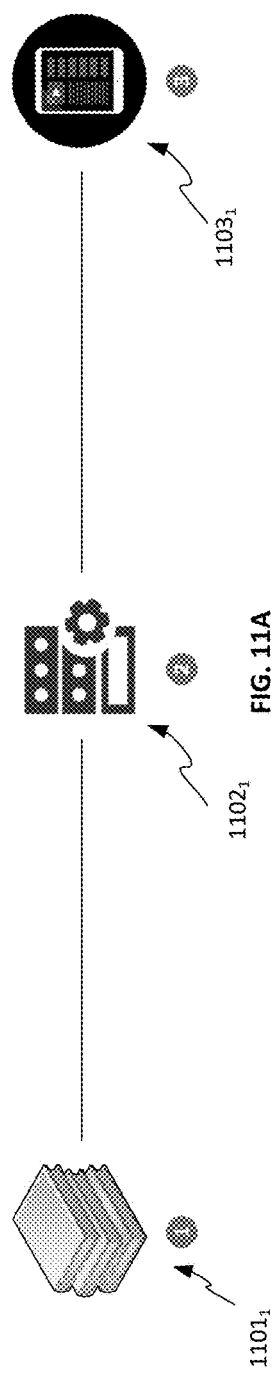
FIGS. 11A and 11B illustratively represent a process for providing curated research in accordance with the disclosure.
Figure 11B:
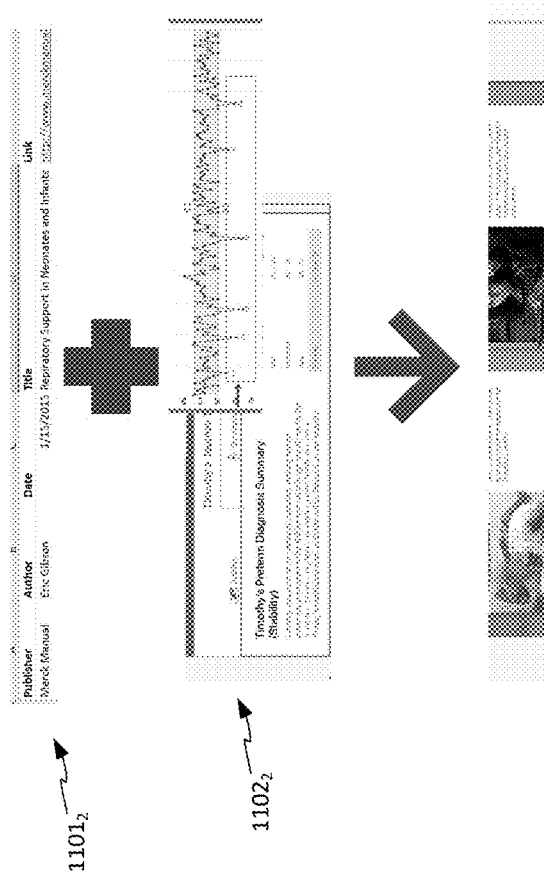

FIGS. 11A and 11B illustratively represent a process for providing curated research in accordance with the disclosure. In one embodiment a research team continuously maintains and updates a research library on specific neonatology topics, ensuring that a library items meet standards, e.g. evidence-based and up-to-date (stage 1101). Algorithms executed by the research curator 132 analyze the baby's medical data from its E.H.R. 162, including diagnosis and recent biostatistics (stage 1102). These data points are matched to research content that specifically addresses the most relevant health topics. The research curator 132 then cooperates with the data visualization and engagement module 112 to suggest curated research to parents via the user interface 208 (stage 1103).

Figure 12:
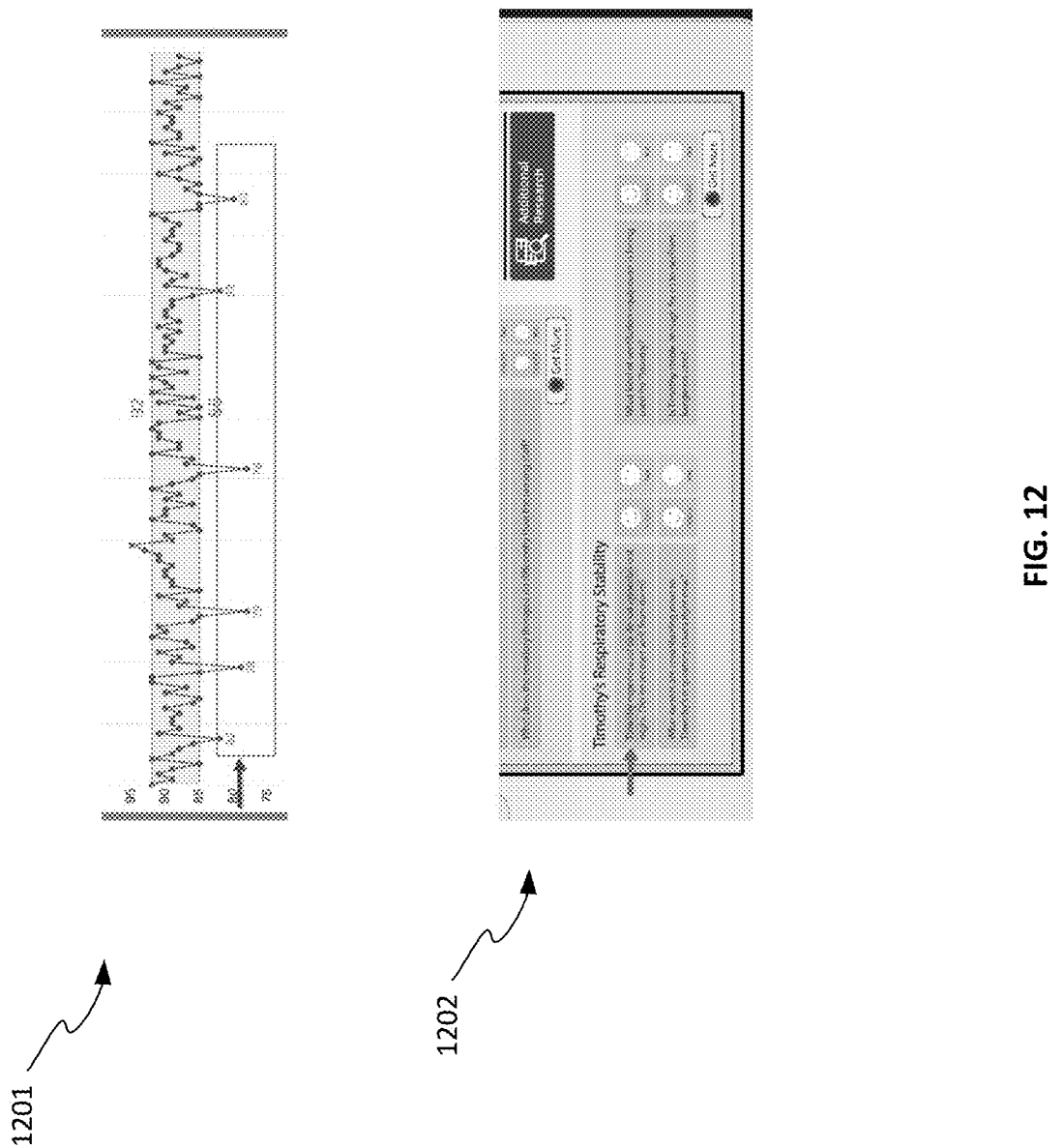
FIG. 12 illustrates a process for tailored question generation in accordance with the disclosure.

Turning now to FIG. 12, a process for tailored question generation in accordance with the disclosure is illustrated. First, the tailored question generator 136 analyzes a baby's actual health data (e.g., as included in the baby's E.H.R. 162) and generates a list of properly articulated questions for parents to ask their baby's healthcare team (stage 1201). The articulated questions are then displayed via the user interface 208 along with a selectable comprehension indicator (state 1202).

Figure 13:
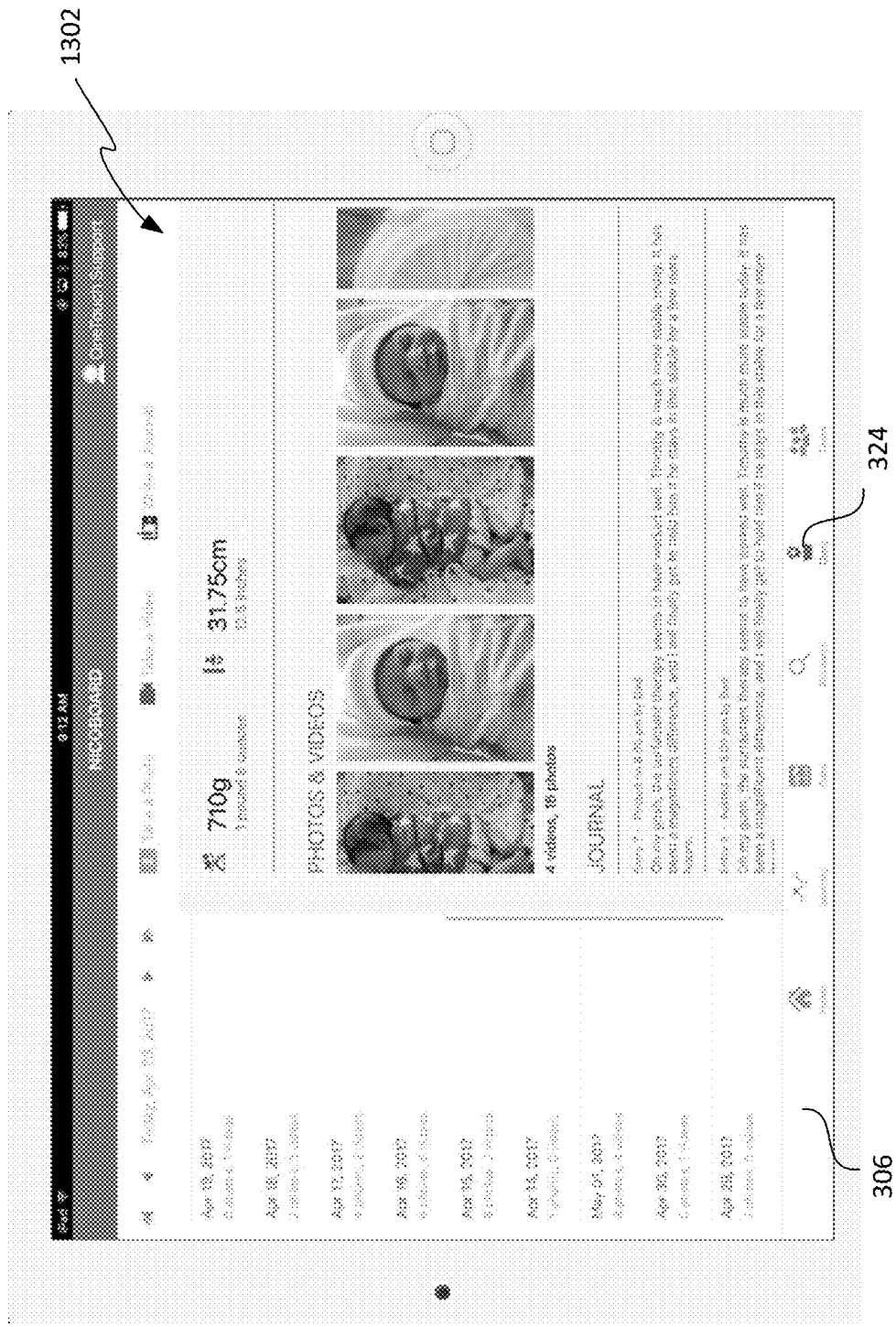
FIG. 13 illustrates an exemplary diary screen which may be reached through selection of a diary icon within a menu ribbon.

FIG. 13 illustrates an exemplary diary screen 1302 which may, for example, be reached through selection of the diary icon 324 within the menu ribbon 306. Through the diary screen 1302 parents can snap photographs and shoot videos using the device 102. In addition, parents and family can enter journal entries in free form. Data such as height and weight can be entered manually by parents. All of these items are cataloged by date for easy sharing and organization of memories.

Exemplary Infrastructure Implementation

Figure 14:
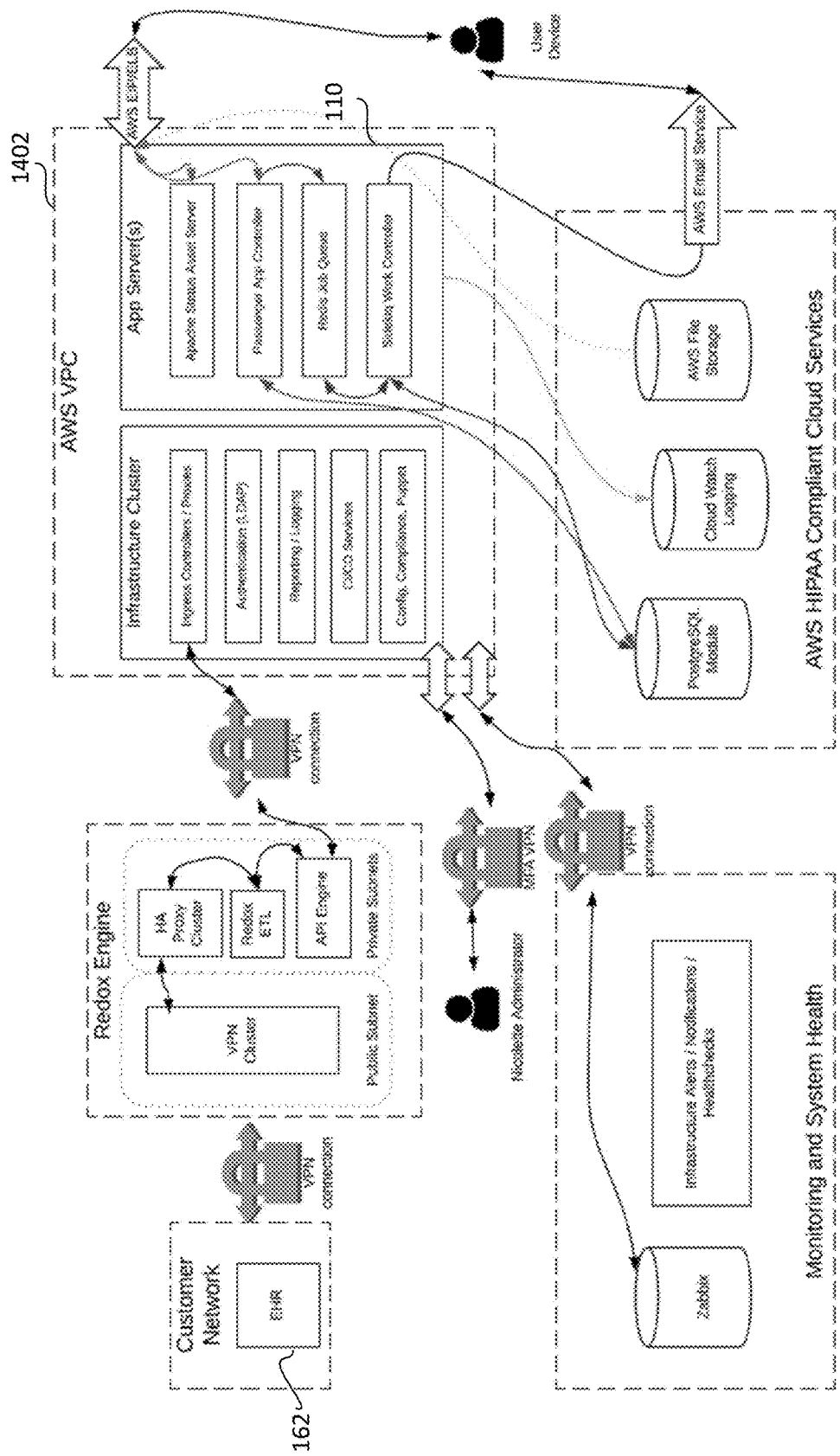
FIG. 14 illustrates an infrastructure architecture diagram of an embodiment of a configuration server within an Azure Virtual Private Cloud (VPC).

FIG. 14 illustrates an infrastructure architecture diagram of an embodiment of the configuration server 110 within an Azure Virtual Private Cloud (VPC) 1402. As shown, in this embodiment the configuration server 110 is linked to a health care facility through a site-to-site VPN through which electronic health records 162 may be accessed.

Figure 15:
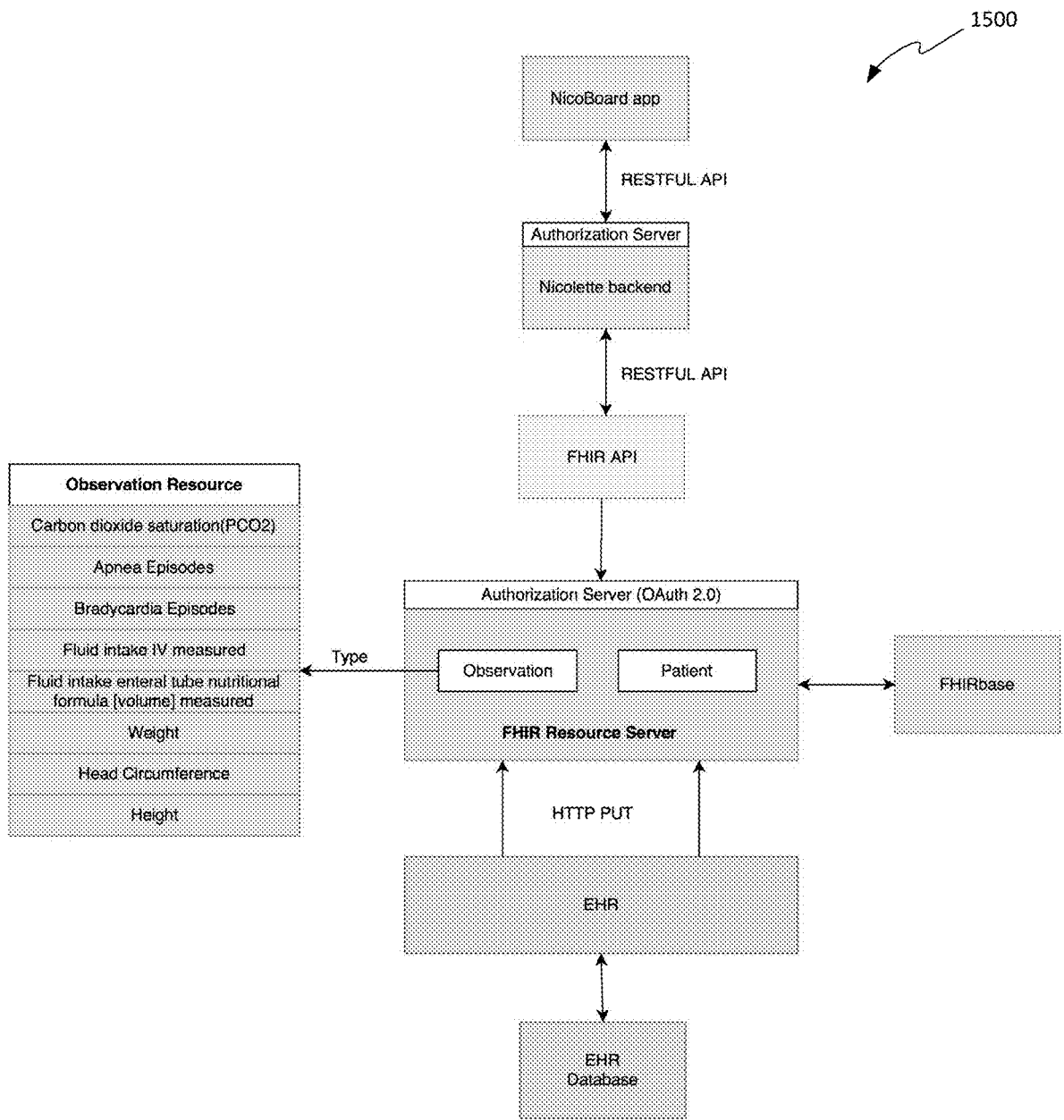
FIG. 15 illustrates an exemplary implementation of a data visualization and engagement platform in accordance with the disclosure.

FIG. 15 illustrates an exemplary implementation of a data visualization and engagement platform 1500 in accordance with the disclosure. As shown, in the embodiment of FIG. 15 the platform utilizes a Fast Healthcare Interoperability Resources (FHIR) Resource Server.

Figure 16:
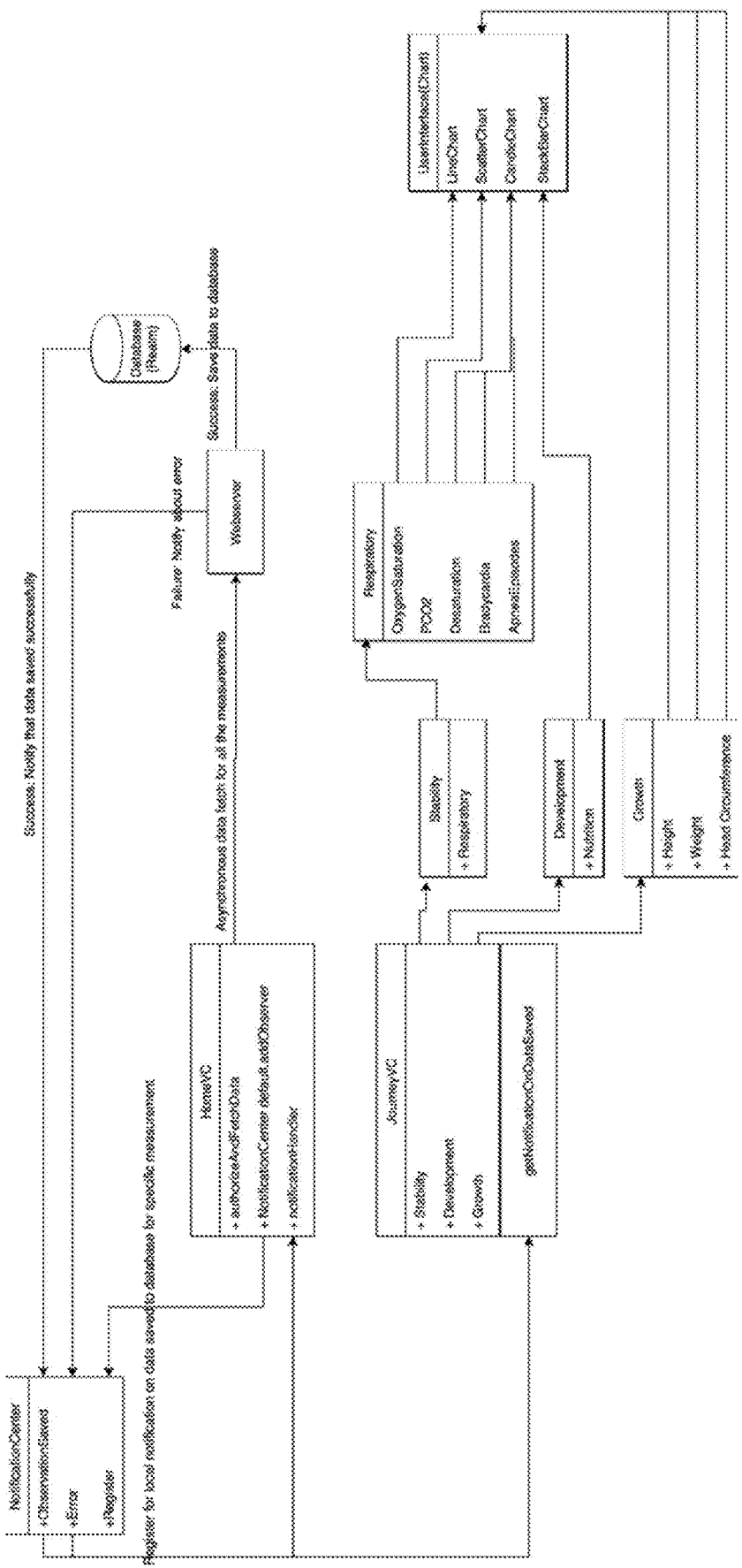
FIG. 16 is a walkthrough diagram illustrating general operation of a data visualization and engagement platform in accordance with the disclosure.

FIG. 16 is a walkthrough diagram illustrating general operation of a data visualization and engagement platform in accordance with the disclosure.

Figure 17:
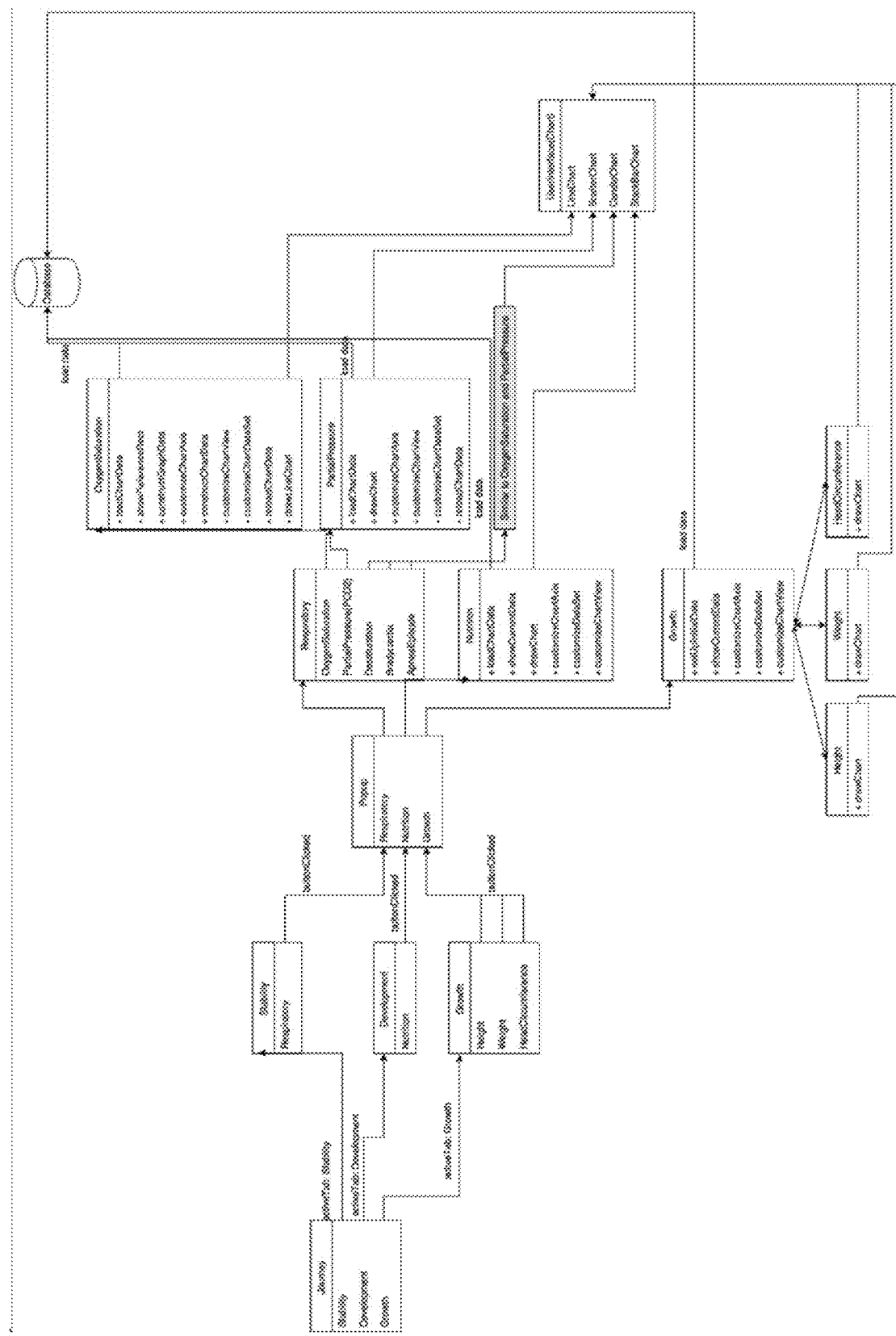
FIG. 17 is a walkthrough diagram illustrating operation of a journey feature of the novel data visualization and engagement platform.

FIG. 17 is a walkthrough diagram illustrating operation of a journey feature of the novel data visualization and engagement platform.

Summary of Specific Features & Processes

Application Format—The Journey

The Journey feature described herein is unique to the market in its ability to exponentially empower patients and families to participate in healthcare decisions. This is achieved in three ways:

(a) Chunking: Chunking is the breaking of a specific healthcare journey into chunks in a way that enables the patient and their advocates to understand the battle quickly. In the case of a NICU family, the platform 100 chunks the NICU experience into three categories: stability, development, and growth.

(b) Layering: Information within each chunk is delivered in layers, which users can add on as they are ready to do so. This enables engagement of users consistently across a lengthy journey, regardless of proficiency with data, language, or medical topics.

(c) Proximity: The tools by which a patient or family can be empowered to participate and make competent decisions are today disparate; separate, difficult processes are required for obtaining and comprehending medical data, performing research, and documenting the healthcare battle. The Journey design of the platform 100 puts visualized data, research & education, and engagement tools all within one touch of the other, enabling rapid comprehension of status, conditions, and treatments while also encouraging greater participation levels.

Visualizing Data for Patients, Parents & Families (a) Principles for Medical Data Visualization: Today, a patient's medical data is difficult to comprehend and use because it is only available in its native format, i.e. raw data, raw notes, and difficult to read formatting. The platform 100 enables rapid comprehension of complex medical through two principles: visualization and context.

(i) Visualizing Data:

(1) Shapes: are used to precisely communicate values without the need for numbers or words. This is what transcends language and education levels.

(2) Colors: Color and shade levels are used to contrast multiple data types displayed in the same space, enabling fast comprehension of multiple measures.

(3) Spatial Relationships: The way in which data visualizations are placed in relationship to each other provides meaning around important parameters such as time and change. For example, if lab results are taken several times in one day, the shapes representing these values will be closer together than if there was one value every three days.

(ii) Context: Further, measures in E.H.R. documents today are often displayed with little or no definition and context, making the numbers meaningless. The platform's technology contextualizes data in the following ways:

(1) Range: Range guides are provided that denote whether the measure is within the healthcare team's established range.

(2) Trend: Comparing the current status of a particular measure with past measurements over time enables patients to understand whether or not there is improvement.

(3) Related Data: Measures by themselves, even with range and trend present, still rely on other measures to derive true meaning. For example, in the case of a NICU baby whose blood oxygen level ($SpO_2$) has historically been unstable but over the past day has been within range, it is still important to understand other measures, such as how much oxygen support ($FiO_2$) is required to keep the baby's $SpO_2$ stable. It is a much different story if $FiO_2$ was increased to stabilize the baby than if the baby's SpO$_2$ levels stabilized without increased support.

(4) Risks: It is important to understand what the health risks are for patients when data behaves in certain ways. For example, if FiO$_2$ support is high over an extended period of time, a health conditions called Retinopathy of Prematurity (ROP) can develop. Without risk context, there is not full meaning to data.

(5) Remedies: Actions that can be taken to improve the patient's health or reduce their risk are important to communicate so that patients and their families can competently collaborate with their healthcare team on decisions. This is the final step in making the data truly actionable.

(b) Visualizing Machine Generated Data: Machine-generated data (e.g. a Pulse Oximeter) is unique because of the way it is collected and the purposes it is used for. Therefore, visual representations that are effective must be crafted in a unique way.

(i) Machine Data Characteristics:

(1) Typically used to monitor patient stability metrics, also known as vital signs (2) Produces data at consistent intervals on a constant basis, e.g. a pulse oximeter generates data with each heart beat (ii) Current Limitations:

(1) Because machines are used to monitor stability, machine data only has value in the moment for parents (2) Machine data is generally only summarized in the E.H.R. as a point-in-time value, hence parents have no way of using the E.H.R. to understand overall stability for an extended period of time or to understand stability trends (iii) Data Point Aggregation:

(1) Aggregates all data points and algorithmically displays a single-screen visualization that delivers and objectively true portrait of a baby's stability for a chosen period of time, e.g. a shift.

(2) Provides one-touch navigation to previous time periods, e.g. shifts (c) Visualizing Lab Data (i) Laboratory Data Characteristics and Uses (1) Laboratory analysis is conducted as needed by clinicians for a variety of reasons, and labs may be run only once or multiple times over a specific timespan to establish a trend or pattern (2) Typical uses include: diagnosis of symptoms, evaluation of a baby's response to treatment, establishing a trend for specific health metrics (ii) Limitations on Prior Systems (1) There is little or no context for lab result meanings, e.g. what is being measured, the desired range, the trend, or relationship to treatments. For clinicians with medical expertise these can still be useful, but are not useful to laypeople.

(2) Lab results for the a specific measure, e.g. PCO2, are not formatted in a way that can be viewed over time to easily observe changes (3) Specific measurements are displayed with data points that may not be relevant to the use, e.g. CO2 used to evaluate need for respiratory support but is directly next to glucose level, which is irrelevant to the topic (iii) Viewing of Trends (1) Plots data points for a specific measurement over time, outside of the lab report itself, giving a parent the ability to view trends for one specific measure (2) Enables parents to view longer or short time periods by pinching in or pinching out on a touch-screen.

(d) Visualizing Manually Entered Data (i) Manually Entered Data Characteristics (1) Manually entered data is typically event-driven and carries with it both quantitative and qualitative information (2) Events that drive manual data include medical episodes (e.g. apnea spells) and routine care (e.g. feeding details such as volume, contents, amount by PO vs. gavage)

(ii) Limitations on Prior Systems (1) Medical episodes are logged, but no quantitative analysis is available for them, e.g. counts, trends, and insights (2) Routine care data is only available as a table, and formatted next to other health data by date, so no trends or insights are possible (iii) Event Counting and Trend Identification (1) Provides counts and trends for medical episodes (2) Allows parents to drill down via touch and view specific qualitative log information tied to the count for each time period (3) Routine care data is quantitatively analyzed and visualized by time period.

Automated Curation of Education & Research (a) Leveling: The platform 100 maintains a library of credible, current, and reviewed education and research materials. These materials are leveled into three categories:

(i) Basic Self-Written Summaries: Summaries written and continuously updated by the platform 100 that contain risks, key measurables, treatments, and participation methods for each health topic.

(ii) Medium Depth Summaries: Third party educational materials, both written and in video form, from providers who write and film in accordance with ADA standards.

(iii) Scholarly Research: Peer-reviewed medical journals.

(b) Data Relevance: Based on the patient's recent medical data and key words in the E.H.R., education and research materials are served that are most relevant to the status, conditions, risks, and remedies.

(c) Topic Relevance: Based on the topic being viewed by the user, research is filtered to include those specific topics. For example, if a parent is reading about their baby's respiratory stability, articles relevant to stability (d) User Learning Proficiency: Based on the depth of content the user prefers, suggested research is presented. As users are able comprehend the research they consume, the more incented they are to consume more and subsequently participate in care.

Engagement Tools (a) Diary: The experience of birth complications or prematurity is harrowing and the heavy amount of emotional distress discourages participation in care. The Diary module enables parents to derive joy and empowerment from their NICU journey, even in the toughest of situations. These features comprise the Diary:

(i) Video & Photo Documentation: Parents can snap photos, shoot videos and caption them.

(ii) Journaling: Parents are able to write their thoughts and feeling free form in journal style.

(iii) Data Logging: Simple, fun measurements for parents to manually log are available, e.g. height, weight, kangaroo time, and breast feeding.

(iv) Cataloguing: All content is catalogued together by date based on when it was generated, creating a true diary effect.

(v) Sharing: Currently, parents find it cumbersome to send updates to family and friends. The diary module makes this simple with one-touch sharing to provide their content to their friends and family in either a segmented (i.e. single photo or journal entry) or aggregated way (i.e. an entire day's content).

(b) Question Generator: Patients across the spectrum are typically intimidated by healthcare institutions, and hence tend to take what they are told at face value; few or no questions are asked, and when they are, the responses are not drilled into for total clarity. This leads to non-compliance and suboptimal participation. Empowerment only comes through dialogue with the healthcare team, and to that end, the question generator 136 generates questions for the family to ask, including the following features:

(i) Data Generated Question Articulation: Based on the baby's data, specific questions are tailored and the parent can read them to the healthcare team verbatim, if needed.

(ii) Question Tracking: Parents can track which questions they've asked (iii) Comprehension Tracking: Parents indicate how well they understood the content of the answers they were given.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Although various modules in the different devices are shown to be located in the processors of the device, they can also be located/stored in the memory of the device (e.g., software modules) and can be accessed and executed by the processors. Accordingly, the specification is intended to embrace all such modifications and variations of the disclosed embodiments that fall within the spirit and scope of the appended claims.

The various methods or processes outlined herein may be coded as software that is executable on one or more processors that employ any one of a variety of operating systems or platforms. Additionally, such software may be written using any of a number of suitable programming languages and/or programming or scripting tools, and may be compiled as executable machine language code or intermediate code that is executed on a framework or virtual machine.

In this respect, various inventive concepts may be embodied as a non-transitory computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The non-transitory computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

In addition, data structures may be stored in non-transitory computer-readable media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish a relationship between information in fields of a data structure, including through the use of pointers, tags or other mechanisms that establish relationship between data elements.

In addition, various inventive concepts may be embodied as one or more methods, of which an example has been provided. The acts performed as part of the method may be ordered in any suitable way. Accordingly, embodiments may be constructed in which acts are performed in an order different from illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A wireless device for facilitating visualization of a state of a patient being monitored by monitoring equipment, the device comprising:
    a wireless network interface;
    a camera;
    a touch-sensitive display;
    a processor in communication with the wireless network interface, the camera and the touch-sensitive display over a system bus; and
    a memory including program instructions which, when executed by the processor, cause to processor to:
        send, to a data visualization server via the wireless network interface, a request for visualization data;
        receive, from the data visualization server via the wireless network interface, visualization data representative of a state of a first physiological parameter of a patient over a first time interval wherein the visualization data includes a first plurality of visualization data values representative of the first physiological parameter and wherein the first plurality of visualization data values is generated by a data visualization module of the data visualization server by aggregating a second plurality of machine data values produced by monitoring equipment when monitoring the first physiological parameter wherein each of the first plurality of visualization data values is representative of the first physiological parameter and is generated by the data visualization module from multiple values of the second plurality of machine data values produced by the monitoring equipment when monitoring the first physiological parameter, wherein the second plurality is greater than the first plurality so as to aggregate a large number of the machine data values produced by the monitoring equipment when monitoring the first physiological parameter into a relatively smaller number of the visualization data values and wherein the data visualization module executes algorithms to synthesize trend data and other metrics from the machine data values produced by the monitoring equipment when monitoring the first physiological parameter and from lab results of the patient in order to translate the machine data values produced by the monitoring equipment when monitoring the first physiological parameter into the visualization data representative of the state of the first physiological parameter of a patient in response to the request;
        display, on the touch-sensitive display, a single monitoring screen wherein a first portion of the single monitoring screen includes a first graphical representation of the visualization data over the first time interval;
        display, on the touch-sensitive display, an additional monitoring screen different from the single monitoring screen wherein the additional monitoring screen includes a second graphical representation including a plurality of graphical objects respectively corresponding to a plurality of time periods and wherein the first time interval is included among the plurality of time periods, each of the graphical objects identifying a high value and a low value of the first physiological parameter over one of the plurality of time periods wherein the high value and the low value associated with each of the plurality of time periods are determined based upon additional machine data values relating to the first physiological parameter produced by the monitoring equipment when monitoring the first physiological parameter during the one of the plurality of time periods.

2. The wireless device of claim 1 wherein the program instructions further include instructions which, when executed by the processor, cause to processor to:
    receive, via the touch-sensitive display, user input corresponding to a change in the time interval;
    display, on the touch-sensitive display, an updated monitoring screen including an updated first graphical representation of the visualization data over an adjusted time interval different from the time interval.

3. The wireless device of claim 1 wherein the program instructions further include instructions which, when executed by the processor, cause to processor to display, in a second portion of the monitoring screen different from the first portion, an icon corresponding to a laboratory measurement of a second physiological parameter of the patient.

4. The wireless device of claim 3 wherein the program instructions further include instructions which, when executed by the processor, cause to processor to:
    receive, via the touch-sensitive display, user input corresponding to selection of the icon corresponding to the laboratory measurement of the second physiological parameter;
    receive, via the wireless network interface, laboratory measurement data representative of a state of the second physiological parameter of the patient over time;

display, via the touch-sensitive display, a laboratory measurement screen wherein a first portion of the laboratory measurement screen includes a graphical representation of the laboratory measurement data;

wherein the second plurality of machine data values and the laboratory measurement data are extracted by one or more modules on the data visualization server from an electronic health record of the patient stored within a database accessible to the data visualization server via an application programming interface (API).

5. The wireless device of claim 1 wherein the program instructions further include instructions which, when executed by the processor, cause to processor to display, via the touch-sensitive display, medical episode information superimposed over the first graphical representation of the visualization data of the state of the first physiological parameter wherein the medical episode information indicates the occurrence of a plurality of medical episodes over the time interval and wherein the plurality of medical episodes are different from events involving the first physiological parameter.

6. The wireless device of claim 5 wherein the first physiological parameter relates to oxygen saturation and the medical episode information relates to at least one of desaturation episodes, apnea episodes and bradycardia episodes and wherein the single monitoring screen displays a plurality of hospital shift icons respectively corresponding to a plurality of hospital shifts, each of the hospital shift icons being selectable in order to cause the single monitoring screen to display additional visualization data relating to the first physiological parameter.

7. The wireless device of claim 1 wherein each of the graphical objects includes numerical information identifying the high value and low value of the physiological parameter over one of the plurality of time periods wherein the numerical information identifying the high value associated with the one of the plurality of time periods represented by the graphical object is located at an upper end of the graphical object and wherein the numerical information identifying the low value associated with the one of the plurality of time periods represented by the graphical object is located at a lower end of the graphical object.

8. The wireless device of claim 7 wherein the program instructions further include instructions which, when executed by the processor, cause to processor to display, via the touch-sensitive display, medical episode information superimposed over the plurality of graphical objects wherein the medical episode information is different from events involving the first physiological parameter.

9. The wireless device of claim 1 wherein the program instructions further include instructions which, when executed by the processor, cause the processor to display, on the touch-sensitive display, one or more range indicators together with the first graphical representation of the visualization data so as to convey an indication, within a width of the single monitoring screen, of stability of the first physiological parameter over the first time interval and wherein the first graphical representation of the visualization data includes a plot of the plurality of visualization data values and wherein the one or more range indicators include a linear representation of at least one of high range value and a low range value.

10. The wireless device of claim 1 wherein the program instructions further include instructions which, when executed by the processor, cause the processor to:

receive manually-entered data relating to events occurring in the care of a patient wherein the one or more events relate to medical episodes;

display another monitoring screen including a representation of a count of the events; and display, in response to user input entered via the touch-sensitive display, an updated monitoring screen including qualitative descriptions of a plurality of the events.

11. The wireless device of claim 1 wherein the program instructions further include instructions which, when executed by the processor, cause to processor to display, via the touch-sensitive display, a plurality of selectable thumbnails wherein user selection of ones of the selectable thumbnails results in display, via the touch-sensitive display, of other graphical representations of the first physiological parameter over other time intervals wherein each of the other time intervals corresponds to different hospital shift.

12. A method for facilitating visualization of a state of a patient being monitored by monitoring equipment, the method comprising:

sending, from a wireless device to a data visualization server, a request for visualization data;

receiving, at the wireless device from the data visualization server, visualization data representative of a state of a first physiological parameter of a patient over a first time interval wherein the visualization data includes a first plurality of visualization data values representative of the first physiological parameter and wherein the first plurality of values of visualization data values is generated by a data visualization module of the data visualization server by aggregating a second plurality of machine data values produced by monitoring equipment when monitoring the first physiological parameter wherein each of the first plurality of visualization data values is representative of the first physiological parameter and is generated by the data visualization module from multiple values of the second plurality of machine data values produced by the monitoring equipment when monitoring the first physiological parameter, wherein the second plurality is greater than the first plurality so as to aggregate a large number of the machine data values produced by the monitoring equipment when monitoring the first physiological parameter into a relatively smaller number of the visualization data values and wherein the data visualization module executes algorithms to synthesize trend data and other metrics from the machine data produced by the monitoring equipment when monitoring the first physiological parameter and from lab results of the patient in order to provide the visualization data in response to the request;

displaying, on a touch-sensitive display of the wireless device, a single monitoring screen wherein a first portion of the single monitoring screen includes a first graphical representation of the visualization data over the time interval;

displaying, on the touch-sensitive display, one or more range indicators together with the first graphical representation of the visualization data so as to convey an indication, within a width of the single monitoring screen, of stability of the first physiological parameter over the first time interval;

receiving, through the touch-sensitive display, user input corresponding to an adjustment in the time interval;

displaying, on the touch-sensitive display, an updated monitoring screen including an updated graphical representation of the visualization data over an adjusted time interval different from the first time interval; and displaying, on the touch-sensitive display, an additional monitoring screen different from the single monitoring screen wherein the additional monitoring screen includes a second graphical representation including a plurality of graphical objects respectively corresponding to a plurality of time periods and wherein the first time interval is included among the plurality of time periods, each of the graphical objects identifying a high value and a low value of the first physiological parameter over one of the plurality of time periods wherein the high value and the low value associated with each of the plurality of time periods are determined based upon additional machine data values relating to the first physiological parameter produced by the monitoring equipment when monitoring the first physiological parameter during the one of the plurality of time periods.

13. The method of claim 12 further including:

receiving, at the wireless device from the data visualization server, manually-entered data relating to events occurring in the care of a patient wherein the events relate to at least one of medical episodes and routine care;

displaying an additional monitoring screen including a representation including a plurality of graphical objects respectively corresponding to a plurality of time periods, each of the graphical objects indicating a count of a number of first of the events occurring within one of the plurality of time periods; and displaying, in response to user input entered via the touch-sensitive display, an updated monitoring screen including qualitative log information associated with the count indicated by a one of the graphical objects selected by the user input.

14. The method of claim 12, further including:

displaying, in a second portion of the monitoring screen different from the first portion, an icon corresponding to a laboratory measurement of a second physiological parameter of the patient.

15. The method of claim 12 wherein the second plurality of machine data values and lab data corresponding to the lab results are extracted by one or more modules on the server from an electronic health record of the patient stored within a database accessible to the data visualization server via an application programming interface (API).

16. The method of claim 15 further including displaying, via the touch-sensitive display, medical episode information superimposed over the plurality of graphical objects wherein the medical episode information is different from events involving the first physiological parameter.

17. The method of claim 12 further including displaying, via the touch-sensitive display, medical episode information superimposed over the graphical representation wherein the medical episode information is different from events involving the first physiological parameter.

18. The method of claim 17 wherein the first physiological parameter relates to oxygen saturation and the medical episode information relates to at least one of desaturation episodes, apnea episodes and bradycardia episodes.

19. The method of claim 12 further including:

analyzing at least the machine data produced by the monitoring equipment in order to generate a natural language summary of medical episode information;

displaying the natural language via the touch-sensitive display.

20. The method of claim 19 further including displaying, via the touch-sensitive display, one or more questions relating to the medical episode information wherein the one or more questions are intended to be addressed to a health care provider associated with the patient.

21. The method of claim 19 wherein the medical episode information relates to at least one of desaturation episodes, apnea episodes and bradycardia episodes.

22. The method of claim 12 further including:

analyzing at least the machine data produced by the monitoring equipment;

determining, based upon the machine data and a medical diagnosis associated with the patient, research content of relevance to the patient; and displaying information relating to the research content via the touch-sensitive display.

* * * * *